United States Patent
Passeron et al.

(10) Patent No.: US 10,983,134 B2
(45) Date of Patent: Apr. 20, 2021

(54) PROTEINS OF THE WNT SIGNALING PATHWAY AND USES THEREOF IN THE DIAGNOSTIC AND TREATMENT OF HYPOPIGMENTATION DISORDERS

(71) Applicants: INSERM (INSTITUT NATIONAL DE LA SANTÉ ET DE LA RECHERCHE MÉDICALE), Paris (FR); UNIVERSITE DE NICE SOPHIA ANTIPOLIS, Nice (FR); CHU DE NICE, Nice (FR)

(72) Inventors: Thierry Passeron, Nice (FR); Florence Joly, Biot (FR)

(73) Assignees: INSERM (INSTITUT NATIONAL DE LA SANTÉ ET DE LA RECHERCHE MÉDICALE), Paris (FR); UNIVERSITÉ CÔTE D'AZUR, Nice (FR); CHU DE NICE, Nice (FR)

( * ) Notice: Subject to any disclaimer, the term of this patent is extended or adjusted under 35 U.S.C. 154(b) by 454 days.

(21) Appl. No.: 15/536,332

(22) PCT Filed: Dec. 16, 2015

(86) PCT No.: PCT/EP2015/080066
§ 371 (c)(1),
(2) Date: Feb. 7, 2018

(87) PCT Pub. No.: WO2016/097035
PCT Pub. Date: Jun. 23, 2016

(65) Prior Publication Data
US 2018/0180631 A1    Jun. 28, 2018

(30) Foreign Application Priority Data

Dec. 18, 2014   (EP) .................................. 14307089

(51) Int. Cl.
| | | |
|---|---|---|
| *A61K 31/422* | (2006.01) | |
| *G01N 33/68* | (2006.01) | |
| *G01N 33/50* | (2006.01) | |
| *A61K 31/506* | (2006.01) | |
| *A61K 33/14* | (2006.01) | |
| *C12Q 1/6883* | (2018.01) | |

(52) U.S. Cl.
CPC ....... *G01N 33/6893* (2013.01); *A61K 31/422* (2013.01); *A61K 31/506* (2013.01); *A61K 33/14* (2013.01); *C12Q 1/6883* (2013.01); *G01N 33/5008* (2013.01); *G01N 33/5023* (2013.01); *C12Q 2600/118* (2013.01); *C12Q 2600/136* (2013.01); *C12Q 2600/158* (2013.01); *G01N 2800/207* (2013.01); *G01N 2800/52* (2013.01); *G01N 2800/56* (2013.01)

(58) Field of Classification Search
CPC .......... G01N 33/6893; G01N 33/5023; G01N 2800/207; G01N 2800/52; G01N 2800/56; G01N 33/5008; A61K 31/422; A61K 31/506; A61K 33/14; C12Q 1/6883; C12Q 2600/118; C12Q 2600/136; C12Q 2600/158
See application file for complete search history.

(56) References Cited

U.S. PATENT DOCUMENTS 7,368,131 B2 *   5/2008   VanStockum ........ A61K 31/195
                                                     424/630

FOREIGN PATENT DOCUMENTS

| KR | 2011 0130282 A | 12/2011 |
|---|---|---|
| KR | 2013 0073069 A | 4/2013 |
| WO | 2006/07886 A2 | 7/2006 |

OTHER PUBLICATIONS

Krugluger et al, Journal of Cosmetic, Dermatological Sciences and Applications, 1, 25-29 (Year: 2011).*
Wan et al, Mol Cell Biochem, 354, 241-246 (Year: 2011).*
Zhong et al, Mol Biosyst., November; 5(11): 1356-1360 (Year: 2009).*
Saito et al, Pigment Cell Research, vol. 16, issue 3, 261-265 (Year: 2003).*
Takaaki et al: "Wnt/ [beta] -Catenin and Kit Signaling Sequentially Regulate Melanocyte Stem Cell Differentiation in UVB-Induced Epidermal Pigmentation", Journal of Investigative Dematology, vol. 133, No. 12, Dec. 1, 2013, pp. 2753-2762.
Kingo K et al: "Expressional changes in the intracellular melanogenesis pathways and their possible role the pathogenesis of vitiligo", Journal of Dermatological Science, Elsevier Science Publishers, Shannon, IE, vol. 52, No. 1, Oct. 1, 2008 pp. 39-46.
Richard Yu et al: "Transcriptome Analysis Reveals Markers of Aberrantly Activated Innate Immunity in Vitiligo Lesional and Non-Lesional Skin", Plos One, vol. 7, No. 12, Dec. 10, 2012, p. e51040.

* cited by examiner

*Primary Examiner* — Sudhakar Katakam
(74) *Attorney, Agent, or Firm* — W&C IP

(57) ABSTRACT

The present invention relates to the identification of proteins of the WNT signaling pathway as therapeutic targets of pigmentation disorder and as biomarkers of pigmentation status. The invention in particular relates to products and methods for treating a hypopigmentation disorder. The invention also relates to products and methods for detecting, diagnosing, staging or monitoring the course of hypopigmentation disorder and is particularly suited for human subjects.

6 Claims, 14 Drawing Sheets

A

B

| Ingenuity Canonical Pathways | P value | Count | Genes |
|---|---|---|---|
| Melanocyte Development and Pigmentation Signaling | 4,5E-07 | 9 | TYRP1, ADCY2, MITF, TYR, SOX10, PAX3, KIT, DCT, MC1R |
| Circadian Rhythm Signaling | 1,7E-06 | 6 | PER3, PER1, ARNTL, NR1D1, BHLHE41, CLOCK |
| Wnt/β-catenin Signaling | 3,2E-03 | 7 | TP53, CDH2, CDH3, SOX10, DVL1, TLE4, LEF1 |

A

A

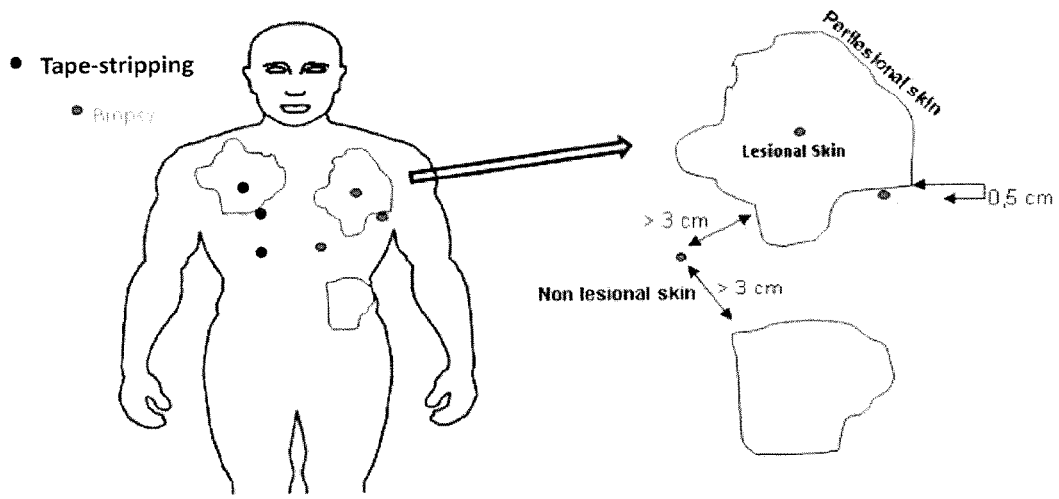

B

| GROUP A healthy | | | GROUP B Vitiligo | | | | |
| --- | --- | --- | --- | --- | --- | --- | --- |
| Age | Gender | Phototype | Age | Gender | Phototype | Location biopsies (Z1) | Location tape-strippings (Z2) |
| 59 | female | II | 64 | Female | II | Left Back Neck | Right Back Neck |
| 33 | female | II | 31 | Female | II | Left Back Wrist | Right Back Wrist |
| 36 | female | V | 40 | Female | V | Left Back Wrist | Right Back Wrist |
| 63 | female | IIIa | 64 | Female | III | Right front hip | Right front trunk axilla |
| 21 | female | IIIa | 19 | Female | III | Left front trunk axilla | Right front trunk axilla |
| 39 | female | VI | 40 | Female | VI | Left Front Chest | Right Front Chest |
| 29 | female | IIIb | 29 | Female | III | Left front trunk axilla | Right front trunk axilla |
| 44 | male | IV | 43 | male | IV | Right front groin | Left front groin |
| 25 | female | IIIa | 25 | Female | III | Left Front periombilical | Right back hip |
| 48 | male | IIIb | 48 | male | III | Right back wrist | Left back wrist |

FIGURE 9

Figure 10:
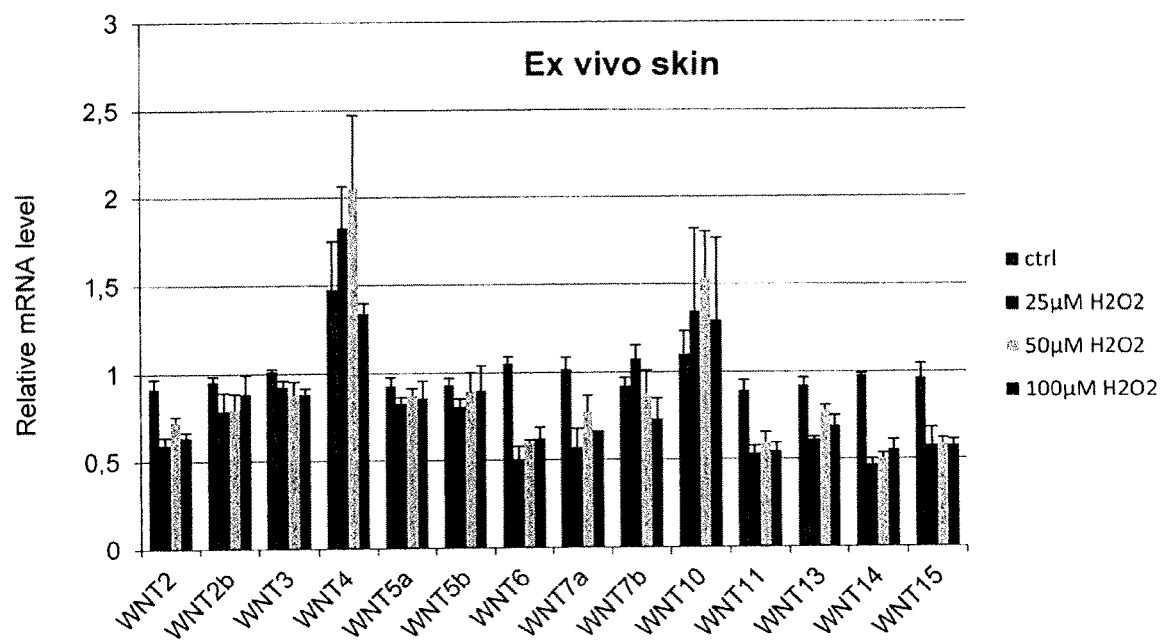

A
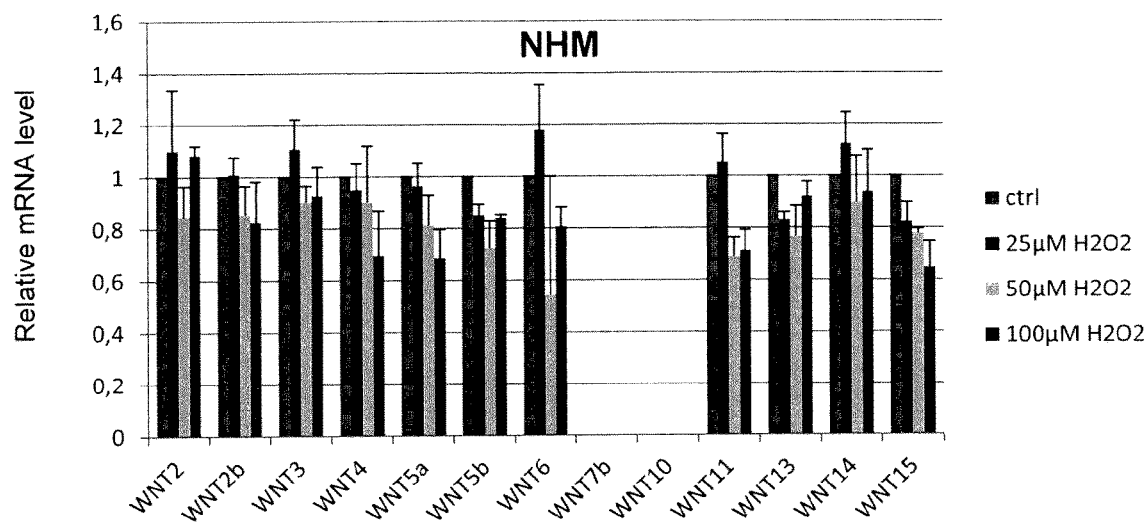
B
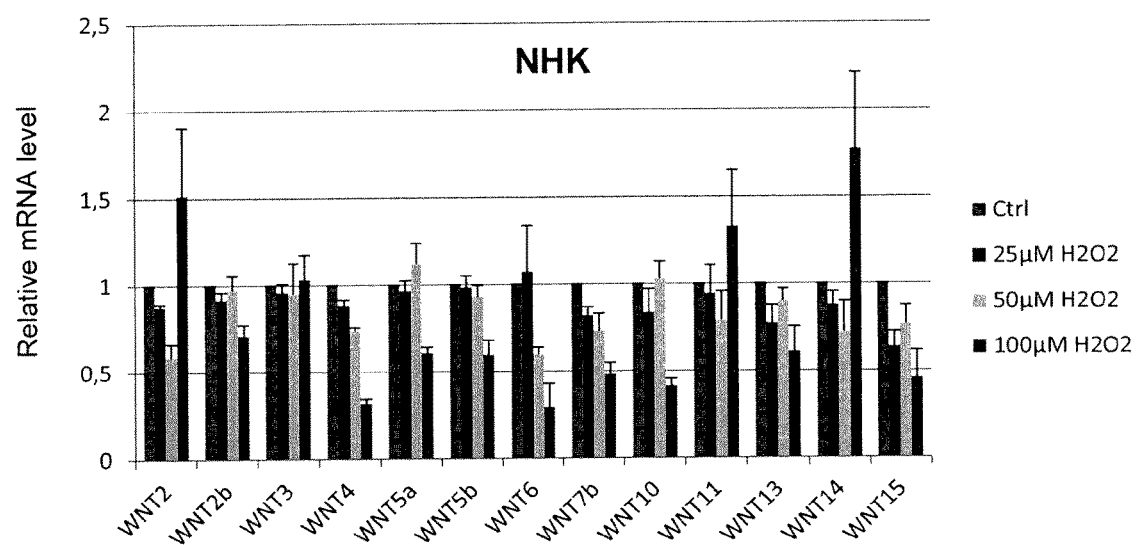
FIGURE 10

PROTEINS OF THE WNT SIGNALING PATHWAY AND USES THEREOF IN THE DIAGNOSTIC AND TREATMENT OF HYPOPIGMENTATION DISORDERS

The present invention relates to the identification of protein of the WNT signaling pathway as therapeutic targets of pigmentation disorders, typically of hypopigmentation disorders, and as biomarkers of pigmentation status. It further relates to corresponding diagnostic and therapeutic applications as well as disease's management applications. The invention in particular relates to products and methods for treating a pigmentation disorder, typically a hypopigmentation disorder such as vitiligo. The invention also relates to products and methods for detecting, diagnosing, staging or monitoring the course of pigmentation disorder, typically a hypopigmentation disorder such as vitiligo, and is particularly suited for human subjects. The invention also relates to binding reagents specific for proteins of the WNT signaling pathway, compositions and devices containing the same, as well as to their uses for pigmentation disorder detection, diagnostic, staging, monitoring, imaging or treatment, as well as for drug development. The present invention more specifically relates to the assessment of a pigmentation disorder, typically a hypopigmentation disorder, using a DNA or a mRNA encoding a protein of the WNT signaling pathway, or the protein itself, as a biomarker.

BACKGROUND

Pigmentation disorders are disturbances of human skin color, either loss or reduction (depigmentation or hypopigmentation) which may be related to loss of melanocytes or to the inability of melanocytes to produce melanin or transport melanosomes correctly, or increase (hyperpigmentation) which is caused by an excessive production of melanin by melanocytes. Melanocytes are located at the lower layer (the stratum basale) of the skin's epidermis, the middle layer of the eye (the uvea), the inner ear, meninges, bones, and heart.

Vitiligo is an acquired depigmentation of the skin inducing a marked alteration of the quality of life of affected individuals. This disease is characterized by destruction of melanocytes that occurs mainly in the skin and results in the appearance of well circumscribed white macules. There are two types of vitiligo, i.e., segmental vitiligo located unilaterally on an area of the face, upper body, legs or arms, which in general does not change; and generalized vitiligo, which has more or less often bilateral symmetrical spots on areas of repeated friction or pressure and may become increasingly important over the years. The exact physiopathological mechanism that leads to the destruction of melanocytes is still elusive, and involves autoimmunity (Passeron T, Ortonne J P 2005; Spritz 2007).

Vitiligo is common and affects 1% to 2% of the general population. For many patients with vitiligo, the disfigurement caused by the disease has a great impact on their quality of life (Ongenae K et al. 2006).

Halting the disease progression and repigmenting the lesional skin represent the two faces of the therapeutic challenge in vitiligo. So far, none of them has been successfully addressed. Oxidative stress and immune system in genetically predisposed individuals participate to the complex pathophysiology of vitiligo.

Currently, there are several therapeutic modalities that can be proposed for the treatment of vitiligo.

Treatments such as narrow-band UVB (Nb-UVB), excimer light, topical steroids, topical tacrolimus or pimecrolimus and combination approaches (with phototherapy and topical steroids or calcineurin inhibitors) can provide cosmetically acceptable repigmentation (>75%) [Lepe, 2003; Ostovari, 2004; Passeron, 2004; Taieb, 2013]. Unfortunately, repigmentation, consisting in vitiligo skin in the differentiation and proliferation of new melanocytes, remains difficult to achieve in most cases. Some localizations, such as hands and feet, are almost impossible to fully repigment with the current approaches. In addition, it is still very difficult to compare the efficacy of different treatment modalities and the results of different studies on the same treatment because: (i) most published studies are uncontrolled; and (ii) there is not a generally accepted biometric tool to assess disease severity and response to treatment. Recently, animal models using reactive T-cells against melanocyte antigens provided interesting data on the immune reaction potentially involved in the depigmentation of vitiligo skin but this model is not adapted to study mechanisms of melanocytes differentiation and repigmentation in vitiligo skin [Mosenson, 2013] [Rashighi, 2014].

In the light of limited therapies and the lack of information about the physiopathology of hypopigmentation disorders such as vitiligo, there is a clear need for identifying new pharmacological markers allowing their correct and early diagnostic as well as their adequate management, and for new therapeutic targets allowing their prevention, attenuation or treatment.

BRIEF DESCRIPTION OF THE INVENTION

Surprisingly, inventors herein demonstrate for the first time that activating or stimulating the WNT pathway allows the repigmentation of depigmented skin lesions, in particular of vitiligo lesions.

A first object of the invention thus relates to an activator of at least one protein of the WNT signaling pathway for use for treating a hypopigmentation disorder such as vitiligo in a subject, typically for repigmenting a hypopigmentation lesion. Herein described is also the use of an activator (agonist) of at least one protein of the WNT signaling pathway for the preparation of a composition for treating hypopigmentation disorder such as vitiligo.

The present invention also relates to the assessment or monitoring of pigmentation status, typically hypopigmentation disorder such as vitiligo, using at least one, for example two, three, four, five or six, protein(s) of the WNT signaling pathway as biomarker(s). The application shows that analysis or measurement of at least one protein of the WNT signaling pathway allows the early detection or the follow-up of patients having pigmentation disorder with remarkably high relevancy, robustness, sensitivity and selectivity.

The invention is particularly suited to detect or monitor pigmentation disorders in human subjects, in particular a hypopigmentation disorder such as vitiligo (particularly the different stages of vitiligo).

An object of the invention relates to a method for the in vitro or ex vivo detection, diagnosis or staging of a pigmentation disorder, typically of a hypopigmentation disorder such as vitiligo, in a subject suspected of suffering of a pigmentation disorder, comprising analysing the expression of at least one protein of the WNT signaling pathway in a biological sample from the subject, said analysis providing information on the presence or stage of a pigmentation disorder in the individual.

Another object of the invention relates to a method for the in vitro or ex vivo detection or diagnosis of a hypopigmentation disorder such as vitiligo, comprising the following steps of:

a) analysing the expression of at least one protein of the WNT signaling pathway in a biological sample from a subject suspected of suffering of a pigmentation disorder, b) analysing the expression of the at least one protein of the WNT signaling pathway in a biological sample from a healthy subject, c) comparing the expressions of the at least one protein of the WNT signaling pathway as analysed in steps a) and b), an expression of the at least one protein of the WNT signaling pathway in the biological sample from the subject suspected of suffering of a hypopigmentation disorder lower than the expression of the at least one protein of the WNT signaling pathway in the biological sample from the healthy subject being an indicator of the presence of a hypopigmentation disorder in the individual suspected of suffering of a hypopigmentation disorder, thereby detecting or diagnosing the hypopigmentation disorder.

Another object of the invention relates to a method for monitoring in vitro or ex vivo the course of a hypopigmentation disorder affecting an individual, wherein the method comprises a step of comparing the expression of at least one protein of the WNT signaling pathway in a first biological sample taken from a subject at t0 to the expression of the at least one protein of the WNT signaling pathway in a second biological sample taken from said subject at t1, a decrease of the expression of the at least one protein of the WNT signaling pathway in the sample taken at t1 being an indicator of the progression of the hypopigmentation disorder in said subject and an increase of the expression of the at least one protein of the WNT signaling pathway in the sample taken at t1 being an indicator of the regression of the hypopigmentation disorder in said subject.

A further object of the invention relates to a method for monitoring in vitro or ex vivo the efficacy of a drug or composition for treating a hypopigmentation disorder, comprising comparing the expression of at least one protein of the WNT signaling pathway in a first biological sample from a subject identified as having one or more of the symptoms of a hypopigmentation disorder before any treatment of the hypopigmentation disorder to the expression of the at least one protein of the WNT signaling pathway in a second biological sample of the same subject who has been exposed to a drug or composition for treating a hypopigmentation disorder, an increase in the expression of the at least one protein of the WNT signaling pathway in the second biological sample being an indicator of efficacy of the drug or composition for treating the hypopigmentation disorder, and a decrease or an absence of modulation in the expression of the at least one protein of the WNT signaling pathway in the second biological sample being an indicator of inefficacy of the drug or composition for treating the hypopigmentation disorder.

Also herein described is an in vitro or ex vivo screening method of an activator a protein of the WNT signaling pathway, comprising determining the ability of a drug candidate to increase (activate or stimulate), or on the contrary to decrease or suppress, the expression and/or biological function of the protein of the WNT signaling pathway and if the ability is confirmed the identification of the drug candidate as an activator (agonist), or on the contrary as an inhibitor (antagonist), of the protein of the WNT signaling pathway.

Another in vitro or ex vivo screening method of modulators of a protein of the WNT signaling pathway, preferably activators, comprises the following steps of:

a) contacting a biological sample exhibiting a hypopigmentation disorder lesion, a biological sample exhibiting the healthy condition, or a mixture of said samples, with one or more drug candidates to be tested;

b) detecting the expression and/or biological function of a protein of the WNT signaling pathway in the biological samples or mixture of samples of step a) and comparing said expression or biological function with the expression or biological function of the protein of the WNT signaling pathway in a sample which has not been contacted with the one or more drug candidates;

c) selecting as modulators drug candidates which activate or stimulate (activators), or on the contrary which decrease or suppress (inhibitors), the expression and/or biological function of the protein of the WNT signaling pathway as measured in the samples or mixtures obtained in the end of step a).

The invention also relates to kits or devices suitable for implementing the above methods, for example a device comprising at least one complementary nucleic acid, antibody, fragment or derivative thereof that binds a protein of the WNT signaling pathway or a nucleic acid coding for such a protein immobilized on a support.

The invention also relates to compositions comprising an inhibitor of a protein of the WNT signaling pathway as herein described and to therapeutic or diagnostic uses thereof.

DETAILED DESCRIPTION OF THE INVENTION

A challenge in the treatment of pigmentation disorders is the lack of efficient molecules allowing efficient differentiation and proliferation of new melanocytes in depigmented area of the skin (including hands and feet), typically in vitiligo lesions, of a subject.

Another challenge is the lack of early, pre-symptomatic detection as visible symptoms of the disorders generally present at advanced stages.

The Wnt signaling pathways are a group of signal transduction pathways made of proteins that pass signals from outside of a cell through cell surface receptors to the inside of the cell. Three Wnt signaling pathways have been characterized: the canonical Wnt pathway, the noncanonical planar cell polarity pathway, and the noncanonical Wnt/calcium pathway. All three Wnt signaling pathways are activated by the binding of a Wnt-protein ligand to a Frizzled family receptor, which passes the biological signal to the protein Dishevelled inside the cell. The canonical Wnt pathway leads to regulation of gene transcription, the noncanonical planar cell polarity pathway regulates the cytoskeleton that is responsible for the shape of the cell, and the noncanonical Wnt/calcium pathway regulates calcium inside the cell. Wnt signaling pathways use either nearby cell-cell communication (paracrine) or same-cell communication (autocrine). They are highly evolutionarily conserved, which means they are similar across many species from fruit flies to human.

Wnt signaling was first identified for its role in carcinogenesis, but has since been recognized for its function in embryonic development. The embryonic processes it controls include body axis patterning, cell fate specification, cell proliferation, and cell migration. These processes are necessary for proper formation of important tissues including bone, heart, and muscle.

Here, inventors describe new therapeutic targets for use for treating a hypopigmentation disorder such as vitiligo.

In the context of the present invention, proteins of interest of the WNT pathway are advantageously selected from LEF (Lymphoid enhancer-binding factor), TCF (DNA-binding transcription factor), MITF (Microphthalmia-associated transcription factor), DCT (Dopachrome tautomerase or dopachrome delta-isomerase, tyrosine-related protein 2), PAX3 (transcription factor 3 of the paired box (PAX) family) and BRn2 transcription factor.

These proteins can also be used as biomarkers as they allow specific, reliable and sensitive detection and staging of pigmentation disorders in particular in human subjects (also herein identified as human individuals or human patients).

For the purpose of the present invention, the tem "marker" or "biomarker" designates a biological marker associated with the absence, presence or stage of a particular pathological or physiological state. The biological markers are in particular proteins, mRNAs or DNA.

Unless otherwise specified, LEF designates the LEF gene, the LEF mRNA or the LEF protein as well as any fragment thereof. Specific examples of LEF protein according to the invention include full length LEF protein, in particular LEF1, and any fragment thereof.

Similarly, TCF designates the TCF gene, the TCF mRNA or the TCF protein as well as any fragment thereof. Specific examples of TCF protein according to the invention include full length LEF protein and any fragment thereof. The same is can be said from MITF, DCT, PAX3 and BRn2 transcription factor.

Inventors performed a transcriptome and proteomic analysis on lesional, perilesional and non-depigmented skin of vitiligo patients compared to matched skin controls of healthy subjects. Their results show that the WNT/β-catenin pathway, implicated in melanocytes differentiation, is altered in vitiligo skin. They demonstrated that the oxidative stress decreases WNT expression/activation in keratinocytes and in melanocytes. They developed an ex vivo skin model that remains functional up to 15 days and confirmed the decreased activation of the WNT pathway in human skin subjected to oxidative stress thanks to said model. Finally, using pharmacological agents that activate the WNT pathway and pharmacological agents that inhibit GSK3B, they treated the ex vivo depigmented skins from vitiligo patients and successfully induced the differentiation of resident stem cells into pre-melanocytes thereby allowing repigmentation of vitiligo lesions to occur, even in areas such as hands and feets.

The invention now provides novel therapeutic targets as well as biomarkers, namely proteins of the WNT regulatory pathway, preferably selected from LEF, TCF, MITF, DCT, PAX3, BRn2 and any combination thereof, for clinical applications, typically pigmentation status assessment, in particular hypopigmentation disorder patient detection, diagnosis, treatment, monitoring and management.

Herein described is an activator (agonist) of at least one protein of the WNT signaling pathway for use for treating a hypopigmentation disorder, in particular vitiligo, in a subject. Such an activator is typically for use for repigmenting a hypopigmentation lesion, in particular a vitiligo lesion, for example a vitiligo lesion located in areas such as hands and feets.

Also described is the use of an activator of at least one protein of the WNT signaling pathway for the preparation of a composition for treating an hypopigmentation disorder such as vitiligo, even in areas such as hands and feets.

Such an activator (agonist) of at least one protein of the WNT signaling pathway is advantageously selected from SKL2001, SKL9001, lithium chloride (LiCl), CHIR99021, SB216763, SB415286, and (2'Z,3'E)-6-bromoindirubin-3-oxime (BIO), preferably from LiCl and CHIR99021. A preferred activator is LiCl.

Also herein described is a pharmaceutical composition comprising at least one activator of at least one protein of the WNT signaling pathway as herein described. Such a composition may be formulated into a suitable dosage form using technology well known to those skilled in the art. The pharmaceutical composition can comprise a pharmaceutically acceptable excipient, vehicle or carrier such as those widely employed in the art of drug-manufacturing. For instance, the pharmaceutically acceptable carrier may include one or more of the following agents: solvents such as olive oil, olive oil refined, cottonseed oil, sesame oil, sunflower seed oil, peanut oil, wheat germ oil, soybean oil, jojoba oil, evening primrose oil, coconut oil, palm oil, sweet almond oil, aloe oil, apricot kernel oil, avocado oil, borage oil, hemp seed oil, macadamia nut oil, rose hip oil, pecan oil, hazelnut oil, sasanqua oil, rice bran oil, shea butter, corn oil, camellia oil, grape seed oil, canola oil, castor oil, and combinations thereof, preferably olive oil refined, emulsifiers, suspending agents, decomposers, binding agents, excipients, stabilizing agents, chelating agents, diluents, gelling agents, thickening agent such as beeswax and/or petroleum jelly, preservatives, lubricants, absorption delaying agents, liposomes, antioxidants such as butylhydroxytoluene or butylhydroxyanisole, and the like. Preferably, the pharmaceutical composition is formulated into a topical formulation that can be directly applied to the skin, for example, a skin suffering from vitiligo. The topical formulation suitable for the pharmaceutical composition may be an emulsion, a gel, an ointment, a cream, a patch, an embrocation, an aerosol, a spray, a lotion, a serum, a paste, a foam, or a drop. In one embodiment of this application, the pharmaceutical composition is formulated into an external preparation by admixing the extract according to this application with a base such as those that are well known and commonly used in the art.

In some embodiments, the dosage and the frequency of administration of the pharmaceutical composition according to the herein described application may vary depending on the following factors: the severity of the disease to be treated, the weight, age, physical condition and response of the subject to be treated. In further or additional embodiments, the amount of the active ingredient(s), typically activator(s) of at least one protein of the WNT signaling pathway, in the pharmaceutical composition is in the range of about 0.001 to about 1000 mg/kg body weight/day, for example, about 0.01 to about 500, 300, or 100 mg/kg body weight/day.

Within the context of the invention, the use of at least one protein of the WNT signaling pathway for pigmentation disorder detection, diagnosis, staging or management (typically monitoring of the course of the pigmentation disorder) includes, without limitation, the use of the protein (in any form, soluble or not, full length or not), or of any coding nucleic acids, as a biomarker. This includes, e.g., the use of any reagent to detect or quantify (i) the protein or any variant or mutant thereof, such as splicing variants or polymorphisms, and/or (ii) any nucleic acid encoding said proteins, such as DNA or RNA, said protein and/or nucleic acid levels being correlated to the pigmentation disorder. The term also includes any measure of the expression level of the cited protein, and a comparison of the measured level to a reference or mean value. The measured amount or level or information provides an indication regarding the specified pigmentation disorder in the subject.

A specific object of the invention relates to a method for the in vitro or ex vivo detection, diagnosis or staging of a hypopigmentation disorder in a subject suspected of suffering of a hypopigmentation disorder, comprising analysing the expression of at least one protein of the WNT signaling pathway in a biological sample from the subject, said analysis providing information on the presence or stage of a hypopigmentation disorder in the subject.

Another object of the invention relates to a method for the in vitro or ex vivo detection or diagnosis of a hypopigmentation disorder, comprising the following steps of:

a) analysing the expression of at least one protein of the WNT signaling pathway in a biological sample from a subject suspected of suffering of a hypopigmentation disorder, b) analysing the expression of the at least one protein of the WNT signaling pathway in a biological sample from a healthy subject, c) comparing the expressions of the at least one protein of the WNT signaling pathway as analysed in steps a) and b), an expression of the at least one protein of the WNT signaling pathway in the biological sample from the subject suspected of suffering of a pigmentation disorder lower than the expression of the at least one protein of the WNT signaling pathway in the biological sample from the healthy subject being an indicator of the presence of a hypopigmentation disorder in the subject suspected of suffering of a hypopigmentation disorder, thereby detecting or diagnosing the pigmentation disorder.

In the context of the invention, the subject is an animal, typically a mammal, preferably a human being whatever its age or sex. The biological sample is typically a tissue sample, preferably a skin sample, such as a biopsy, taken from a subject. The biopsy may vary in size and is preferably from 1 to 6 mm in diameter.

According to one particular and preferred embodiment, the sample is a skin sample taken by means of tape stripping, such as with D-Squames, according to the method described in Wong R et al., "*Analysis of RNA recovery and gene expression in the epidermis using non-invasive tape stripping*"; J Dermatol Sci. 2006 November; 44(2):81-92; or in Benson N R, et al., "*An analysis of select pathogenic messages in lesional and non-lesional psoriatic skin using non-invasive tape harvesting*". J Invest Dermatol. 2006 October; 126(10): 2234-41; or else in Wong R et al., "*Use of RT-PCR and DNA microarrays to characterize RNA recovered by non-invasive tape harvesting of normal and inflamed skin*". J Invest Dermatol. 2004 July; 123(1):159-67. According to the principle of tape stripping, the product used comprises a flexible translucent polymer support and an adhesive. The product is applied repeatedly to the skin of the patient, preferably until loss of adhesion. The sample obtained relates only to the content of the outermost layers of the epidermis.

The analysis typically comprises determining the presence, absence or amount of the at least one protein of the WNT signaling pathway, the absence of at least one protein of the WNT signaling pathway or an expression thereof higher than a reference amount being indicative of the presence or stage of a hypopigmentation disorder in the individual.

The expression analysis or detection can be performed by any suitable method, known to those skilled in the art, such as western blotting, IHC, mass spectrometry (Maldi-TOF and LC/MS analyses), radioimmunoassay (RIA), ELISA or any other method known to those skilled in the art or else by assaying the mRNA according to the methods customarily known to those skilled in the art. The techniques based on the hybridization of mRNA with specific nucleotide probes are the most customary [in situ hybridization, FISH, Northern blotting, RT-PCR (Reverse Transcriptase Polymerase Chain Reaction), quantitative RT-PCR (qRT-PCR), RNase protection].

A method for analysing a protein content obtained in particular according to the previously herein described sampling method is described in Patent Application WO2009/068825 (Galderma R&D). Since this method is rapid, non-invasive and relatively inexpensive, it is particularly preferred. Quantification is performed in the skin sample obtained on the flexible and adhesive support in order to detect the at least one protein of the WNT signaling pathway of which the presence, the absence or the variation in amount or in concentration compared with a standard value is associated with the presence, with the progression or with the absence of the (potentially suspected) pigmentation disorder.

In a particular embodiment, analysing at least one protein of the WNT signaling pathway comprises contacting a biological sample, or an aliquot thereof, with a specific binding reagent that binds the at least one protein of the WNT signaling pathway or nucleic acid encoding said protein and determining the presence or amount of the at least one protein of the WNT signaling pathway or of the corresponding nucleic acid bound to said binding reagent.

Selective or specific binding indicates that binding to another molecule can be discriminated from (e.g., occurs with higher affinity or avidity than) specific binding to the target biomarker. Preferred reagents do not bind, under selective condition, to any other unrelated human blood protein but the reference protein. Binding of a reagent to a reference molecule can be tested according to methods well known by the skilled person.

The binding reagent is typically a specific ligand selected from a complementary nucleic acid, an antibody, an aptamer, and a fragment or derivative thereof.

In a particular embodiment, the binding reagent is an antibody. The antibody may be a polyclonal or a monoclonal antibody, most preferably a monoclonal. It may be of various classes (e.g., IgG, IgE, IgM, etc.). The antibody may be of various animal origin, or human or synthetic or recombinant. Furthermore, the term antibody also includes fragments and derivatives thereof, in particular fragments and derivatives of said monoclonal or polyclonal antibodies having substantially the same antigenic specificity. Antibody fragments include e.g., Fab, Fab'2, CDRs, etc. Derivatives include humanized antibodies, human antibodies, chimeric antibodies, poly-functional antibodies, Single Chain antibodies (ScFv), etc. These may be produced according to conventional methods, including immunization of an animal and collection of serum (polyclonal) or spleen cells (to produce hybridomas by fusion with appropriate cell lines).

Methods of producing polyclonal antibodies from various species, including mice, rodents, primates, horses, pigs, rabbits, poultry, etc. are well known from the skilled person. Briefly, the antigen is combined with an adjuvant (e.g., Freud's adjuvant) and administered to an animal, typically by sub-cutaneous injection. Repeated injections may be performed. Blood samples are collected and immunoglobulins or serum are separated.

Methods of producing monoclonal antibodies from various species as listed above may be found, for instance, in Harlow et al. (Antibodies: A laboratory Manual, CSH Press, 1988) or in Kohler et al. (Nature 256 (1975) 495), incorporated herein by reference. Briefly, these methods comprise immunizing an animal with the antigen, followed by a recovery of spleen cells which are then fused with immortalized cells, such as myeloma cells. The resulting hybridomas produce the monoclonal antibodies and can be selected by limit dilutions to isolate individual clones. Antibodies may also be produced by selection of combinatorial libraries of immunoglobulins, as disclosed for instance in Ward et al. (Nature 341 (1989) 544).

Recombinant antibodies, or fragments or derivatives thereof, may be produced by methods known per se in the art, for example by recombination in a host cell, transformed with one or more vectors enabling the expression and/or secretion of the nucleotide sequences encoding the heavy chain or the light chain of the antibody. The vector generally contains a promoter, translation initiation and termination signals, and suitable transcriptional regulatory regions. It is stably maintained in the host cell and may optionally possess specific signals for secretion of the translated protein. These different components are selected and optimized by one of skill in the art according to the host cell used.

In a preferred embodiment, the antibody directed against a protein of the WNT signaling pathway, as well as the fragment or derivative thereof is an antibody, fragment or derivative thereof which binds the human protein of the WNT signaling pathway or a fragment thereof (such as a peptide or epitope).

Particular examples of such antibodies are monoclonal antibodies.

Antibodies may be found or generated against a protein of the WNT signaling pathway and used in the present invention. It should be noted however that the use of antibodies that bind an epitope of a protein of the WNT signaling pathway wherein said binding is at least partially displaced by the corresponding human protein of the WNT signaling pathway is particularly preferred as well as a fragment or derivative of such an antibody having the same antigen specificity.

For use in the invention, the antibodies may be coupled to heterologous moieties, such as labels, tags, linkers, etc., typically to a detectable moiety.

The invention also relates to kits or devices suitable for implementing the above methods.

A typical device comprises at least one specific reagent, typically at least one complementary nucleic acid, antibody, fragment or derivative thereof, that binds a protein of the WNT signaling pathway or a nucleic acid encoding said protein, said specific reagent being immobilized on a support. Preferably the support is a membrane, a slide, a microarray, a chip or a microbead.

A particular kit comprises a device as herein described and at least one reagent to perform, detect or quantify an immune reaction, in particular an antibody-antigen complex.

A further object of the invention relates to a method for monitoring in vitro or ex vivo the course of a hypopigmentation disorder affecting an individual, wherein the method comprises a step of comparing the expression of at least one protein of the WNT signaling pathway in a first biological sample taken from a subject at t0 to the expression of the at least one protein of the WNT signaling pathway in a second biological sample taken from said subject at t1, t1 being posterior to t0, a decrease of the expression of the at least one protein of the WNT signaling pathway in the sample taken at t1 being an indicator of the progression of the hypopigmentation disorder in said individual and an increase of the expression of the at least one protein of the WNT signaling pathway in the sample taken at t1 being an indicator of the regression of the hypopigmentation disorder in said subject.

Another object of the invention relates to a method for monitoring in vitro or ex vivo the efficacy of a drug or composition for treating a hypopigmentation disorder, comprising comparing the expression of at least one protein of the WNT signaling pathway in a first biological sample from a subject identified as having one or more of the symptoms of a hypopigmentation disorder before any treatment of the hypopigmentation disorder to the expression of the at least one protein of the WNT signaling pathway in a second biological sample of the same subject who has been exposed to a drug or composition for treating a pigmentation disorder, an increase in the expression of the at least one protein of the WNT signaling pathway in the second biological sample being an indicator of efficacy of the drug or composition for treating the hypopigmentation disorder, and a decrease or an absence of modulation in the expression of the at least one protein of the WNT signaling pathway in the second biological sample being an indicator of inefficacy of the drug or composition for treating the hypopigmentation disorder.

Also herein described is an in vitro or ex vivo screening method of a modulator of a protein of the WNT signaling pathway, comprising determining the ability of a drug candidate to activate or stimulate, or on the contrary to decrease or suppress, the expression and/or biological function of the protein of the WNT signaling pathway, and, if the ability is confirmed, the identification of the drug candidate as an inhibitor (antagonist), or on the contrary as an activator (agonist), of the protein of the WNT signaling pathway.

Another in vitro or ex vivo screening method of modulators of a protein of the WNT signaling pathway, preferably activators, comprises the following steps of:

a) contacting a biological sample exhibiting a hypopigmentation disorder lesion, a biological sample exhibiting the healthy condition, or a mixture of said samples, with one or more drug candidates to be tested;

b) detecting the expression and/or biological function of a protein of the WNT signaling pathway in the biological samples or mixture of samples of step a) and comparing said expression or biological function with the expression or biological function of the protein of the WNT signaling pathway in a sample which has not been contacted with the one or more drug candidates; and c) selecting as modulators drug candidates which activate or stimulate (activators), or on the contrary which decrease or suppress (inhibitors), the expression and/or biological function of the protein of the WNT signaling pathway as measured in the samples or mixtures obtained in the end of step a).

The identified modulator will influence the biological function of the protein of the WNT signaling pathway or a biological process modulated by this marker. For screening purposes, the biological samples advantageously consist of transfected cells containing reporter genes operating under the control of a promoter (totally or partially) controlling the expression of the gene encoding the protein of the WNT signalling pathway. Alternatively, the promoter may be, at least in part, synthetically assembled and contain adequate responsive elements. The ability of a compound to modulate the function of the gene encoding the protein of the WNT signaling pathway, is evaluated by analyzing the expression of the reporter gene.

The transfected cells may further be engineered to express the protein of the WNT signaling pathway. The reporter gene may encode an enzyme that with its corresponding substrate, provides coloured product(s) such as CAT (chloramphenicol acetyltransferase), GAL (beta galactosidase), or GUS (beta glucuronidase). It might be either luciferase or GFP (Green Fluorescent Protein). Reporter gene protein dosage or its activity is typically assessed by colourimetric, fluorometric or chemoluminescence methods.

The selected modulator, preferably inhibitor or antagonist, can be a polypeptide, a DNA, a RNA, or a PNA ("Peptide nucleic acid", i.e. a DNA-like structure with a polypeptidic chain substituted by purine and pyrimidine bases). Advantageously, the modulator is administered to a patient in a sufficient quantity so as the measure a plasmatic concentration which is from about 0.01 µg/ml to about 100 µg/ml, preferably from about 1 µg/ml to about 5 µg/ml.

Other characteristics and advantages of the invention are given in the following experimental section (with reference to FIGS. 1-11), which should be regarded as illustrative and not limiting the scope of the present application.

FIGURES

Figure 1:
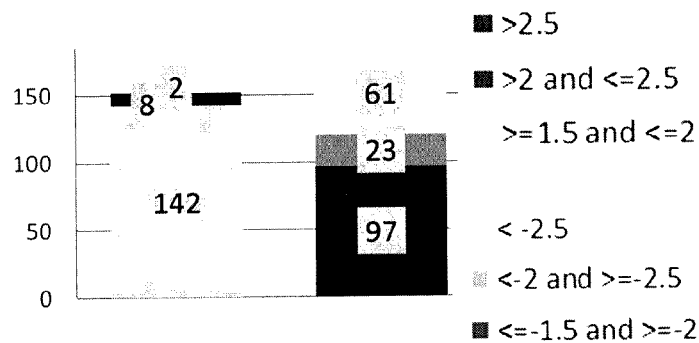

FIG. 1. Transcriptomic analysis of vitiligo patients highlights the disappearance of melanocytes and the involvement of WNT signaling pathway without hint of immune system activation.

(A) Histogram of differentially expressed genes showing that 95% of upregulated transcripts in vitiligo lesional skin has less than 2-fold difference in gene expression when compared to healthy skin.

(B) Ingenuity based canonical pathways enriched in vitiligo lesional skin.

(C) Cluster analysis of microarray data from healthy skin (HS), non lesional (NLS), perilesional (PLS) and lesional skin (LS) from vitiligo subjects. All genes significantly modulated (|FC|≤1.5 P<0.05) were included in this analysis.

Figure 2:
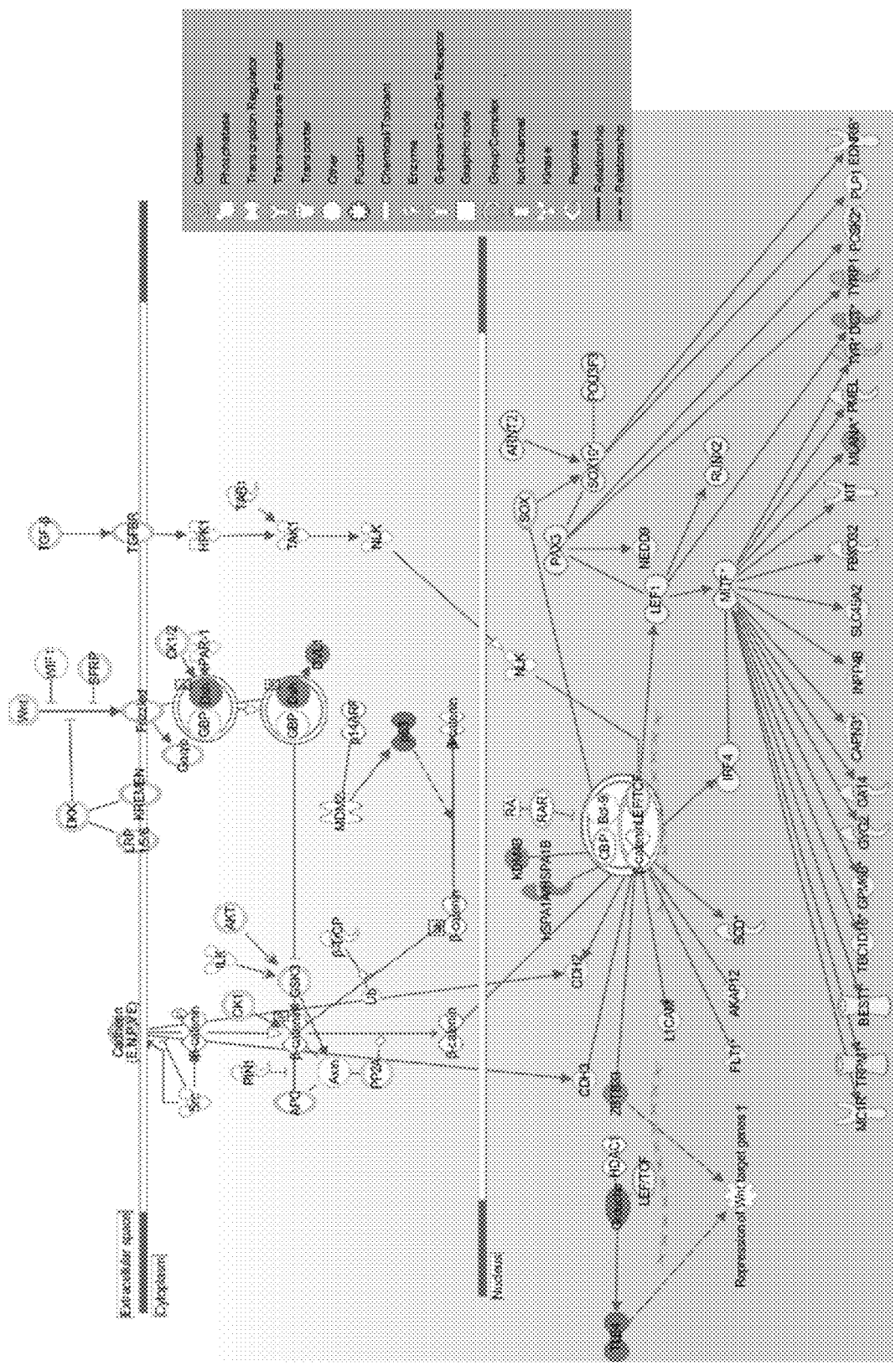

FIG. 2. IPA based analysis of WNT and MITF pathway involvement in vitiligo lesional skin.

A transcriptional network linking Wnt signaling and Melanogenesis pathways. Lesional vitiligo skin is both characterized by a downregulated expression of key transducer of Wnt signaling pathway (E.g. LEF1), and by the upregulation of negative regulators of Wnt signaling pathway such as p53 and TLE4 (groucho family member) and ZBTB33/Kaiso (involved in transcriptional repression of wnt target genes)

LEF1/bCatenin regulates melanogenesis through SOX10 transcriptional induction which in turn regulates the expression of EDNRB, PCSK2 and PLP1 genes. LEF1/bCatenin also directs the transcription of MITF which governs melanogenesis at the transcriptional level. LEF1/bCatenin is also linked to melanogenesis via the IRF4 encoding gene. This transcription factor whose function is still unclear in melanocyte has been shown to cooperate with MITF.

Figure 3:
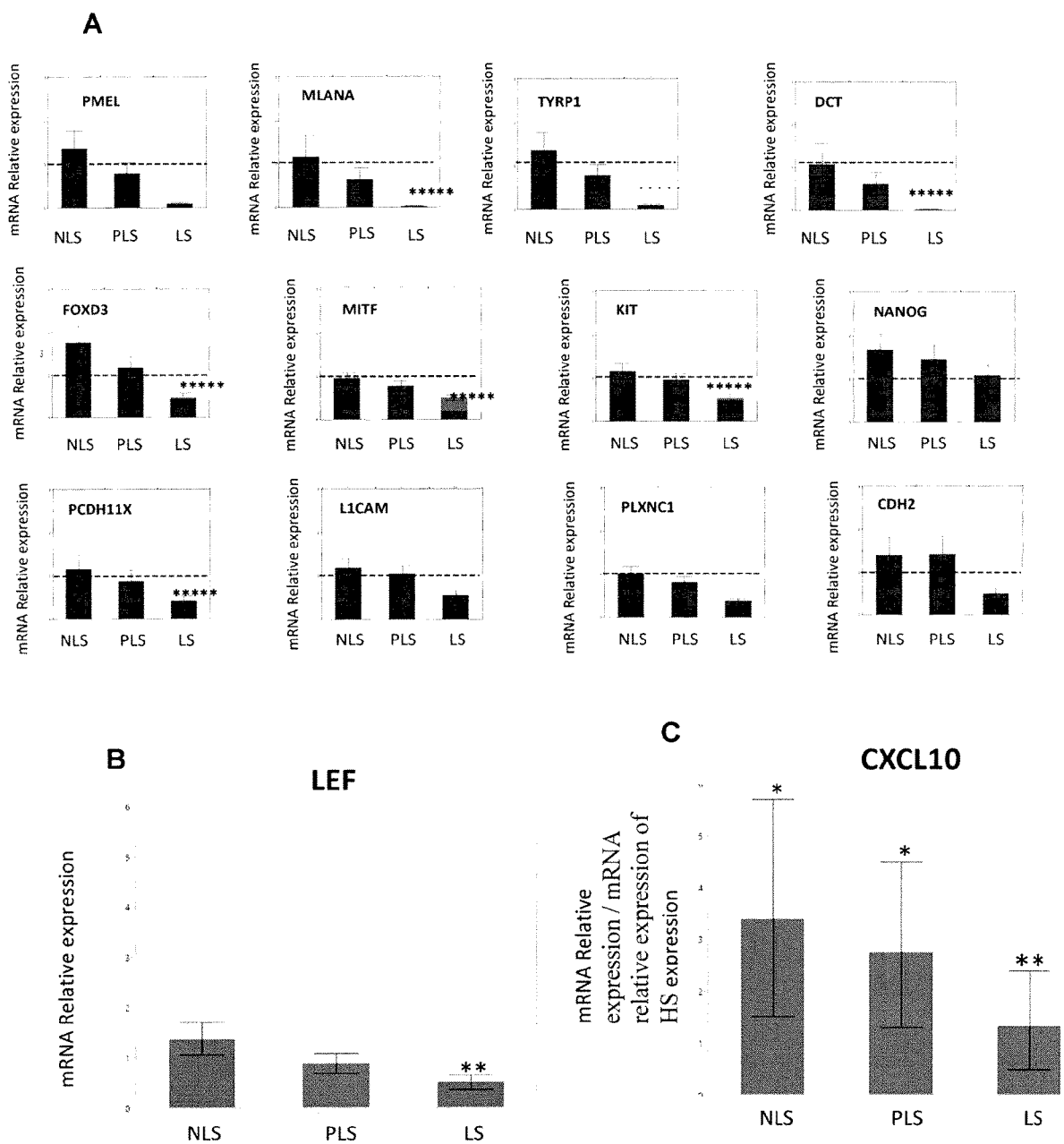

FIG. 3. qRT-PCR validation of loss of melanocytic gene expression: vitiligo lesional skin shows complete loss of expression of genes involved in the terminal differentiation of melanocytes and residual expression of key melanogenic transcription factors or adhesion molecules encoding genes (A).

Gene expression was measured by qRT-PCR and calculated for group analysis, i.e. NLS (Non Lesional Skin) or PLS (Peri-Lesional Skin) or LS (Lesional Skin) group compared to HS group (Healthy Skin) using a T-TEST linear model without pairing. Modulated genes were considered significantly modulated if both the |fold change| was ≥1.8 and the FDR value was <0.05.

The y-axis displays fold change in expression relative to the pool of healthy skin. The data were normalized relative to HPRT, ACTB and GAPDH. The error bars display the standard error of three replicates. *=p<0.05; =p<0.01; *=p<0.001; **=p<0.0001; ***=p<0.00001.

TLDA validation set encompassed both genes related to terminal differentiation markers (PMEL, MLANA, TYRP1, DCT), transcription factors involved in melanogenesis (MITF, FOXD3, KIT, NANOG), and adhesion molecules (PLXNC1, PCDH11X, CDH2 and L1CAM).

qRT-PCR validation of LEF1 mRNA (B) and CXCL10 mRNA (C): LEF1 is selectively decreased in lesional skin samples whereas CXCL10 mRNA is upregulated in non lesional and perilesional skin biopsies compared to healthy skin.

Gene expression was measured by qRT-PCR and calculated for group analysis, i.e. NLS or PLS or LS group compared to HS group (Healthy Skin) using a T-TEST linear model without pairing. Modulated genes were considered significantly modulated if both the |fold change| was ≥1.8 and the FDR value was <0.05. The y-axis displays fold change in expression relative to the pool of healthy skin. The data were normalized relative to HPRT, ACTB and GAPDH. The error bars display the standard error of three replicates. *=p<0.05 **=p<0.005

Figure 4:
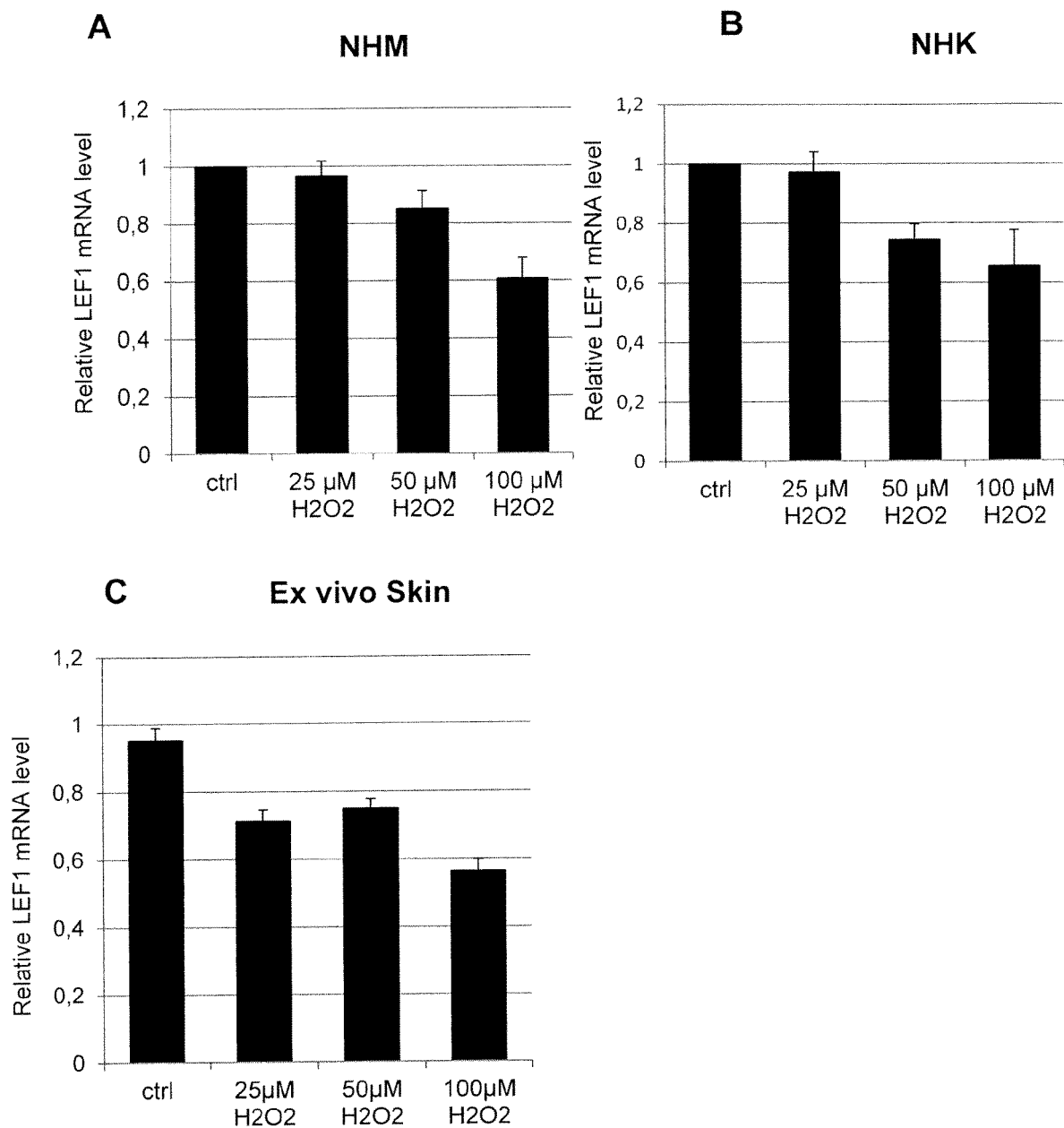

FIG. 4: Oxidative stress decreases WNT pathway in the skin.

NHM (A) and NHK (B) and whole skin in ex vivo culture (C) were stimulated 24 hours with 25 to 100 µM of $H_2O_2$. After mRNA extraction, a reverse transcription was performed and the relative gene expression of LEF1 was analyzed with qPCR.

Figure 5:
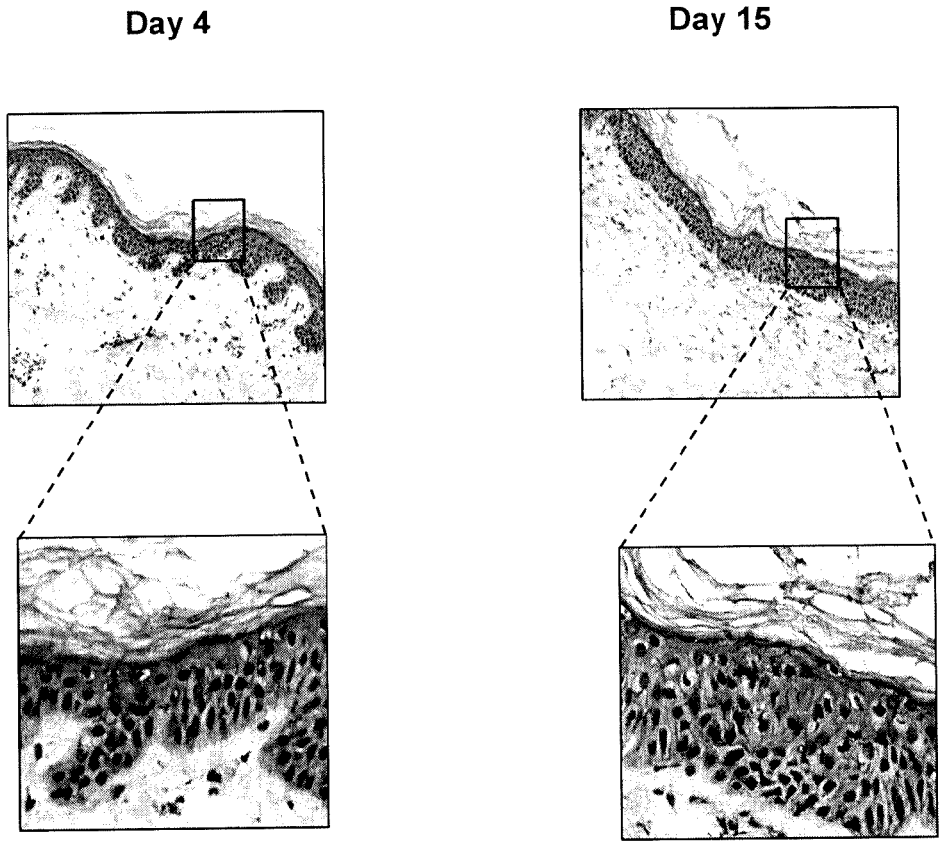
Figure 5:
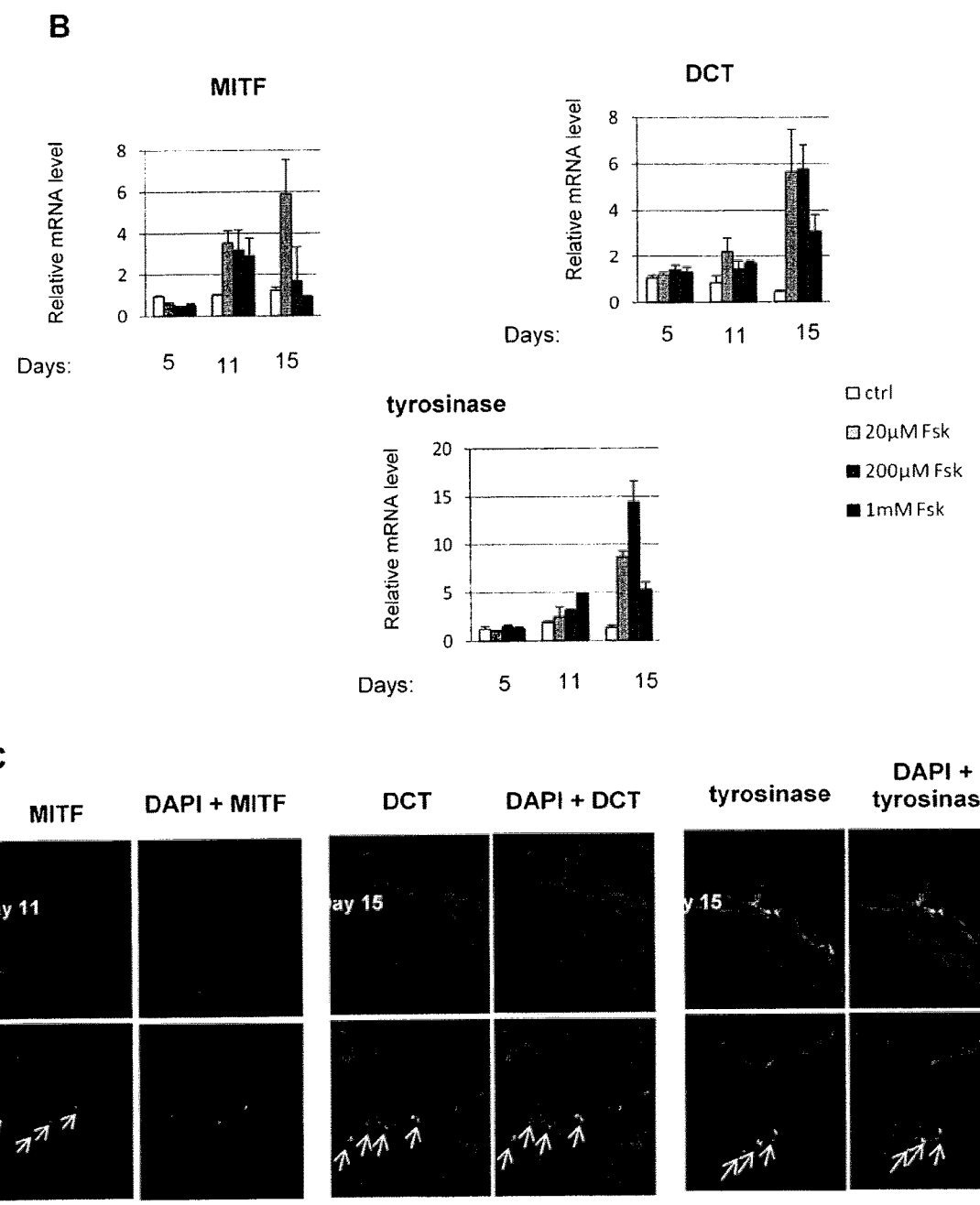

FIG. 5: Development of an ex vivo skin model to study vitiligo skin.

(A) Six mm skin biopsies were obtained from abdominoplasty surgery and were disposed on a transwell chamber to allow a semi-liquid culture environment. The skin was stimulated with 20 µM to 1 mM of forkolin added in the culture medium every second days during 4 to 15 days. After 4, 11 and 15 days, the morphology of the skin was visualized by microscopy with a Hematoxylin—Eosin staining (X20).

(B) The ability of the skin to respond to melanogenic stimuli was assessed using forskolin treatment.

The mRNA was extracted from biopsies and analyzed by RT-qPCR to quantify the expression of melanogenic genes: MITF, DCT and tyrosinase.

(C) An immunohistostaining was performed to study the expression of MITF, DCT and tyrosinase proteins after 11 or 15 days of forskolin stimulation.

Figure 6:
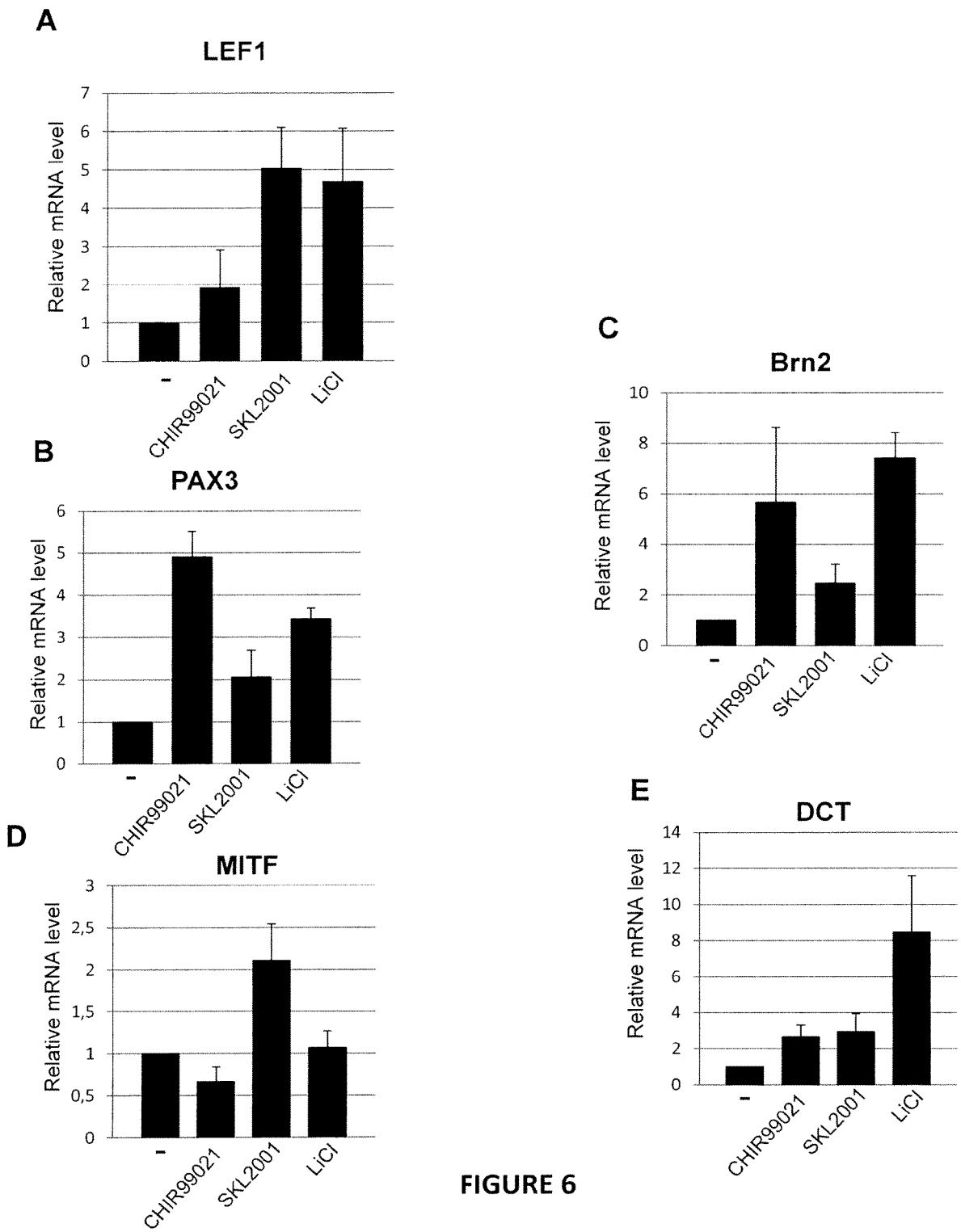

FIG. 6: Pharmacological WNT pathway activators increase WNT pathway in ex vivo vitiligo skin and induce the upregulation of melanoblast markers.

Vitiligo patients (n=9) were biopsied in lesional skin area. The biopsies were stimulated in ex vivo culture during 14 days with GSK3β inhibitor: CHIR99021 (3 µM) or LiCl (20 µM) or with WNT agonist: SKL2001 (40 µM) every other day. mRNA was extracted and a RT-qPCR was performed to quantify the relative expression of LEF (A) and the pre-melanocytes markers PAX3 (B), Brn2 (C) MITF (D) and DCT (E).

Figure 7:
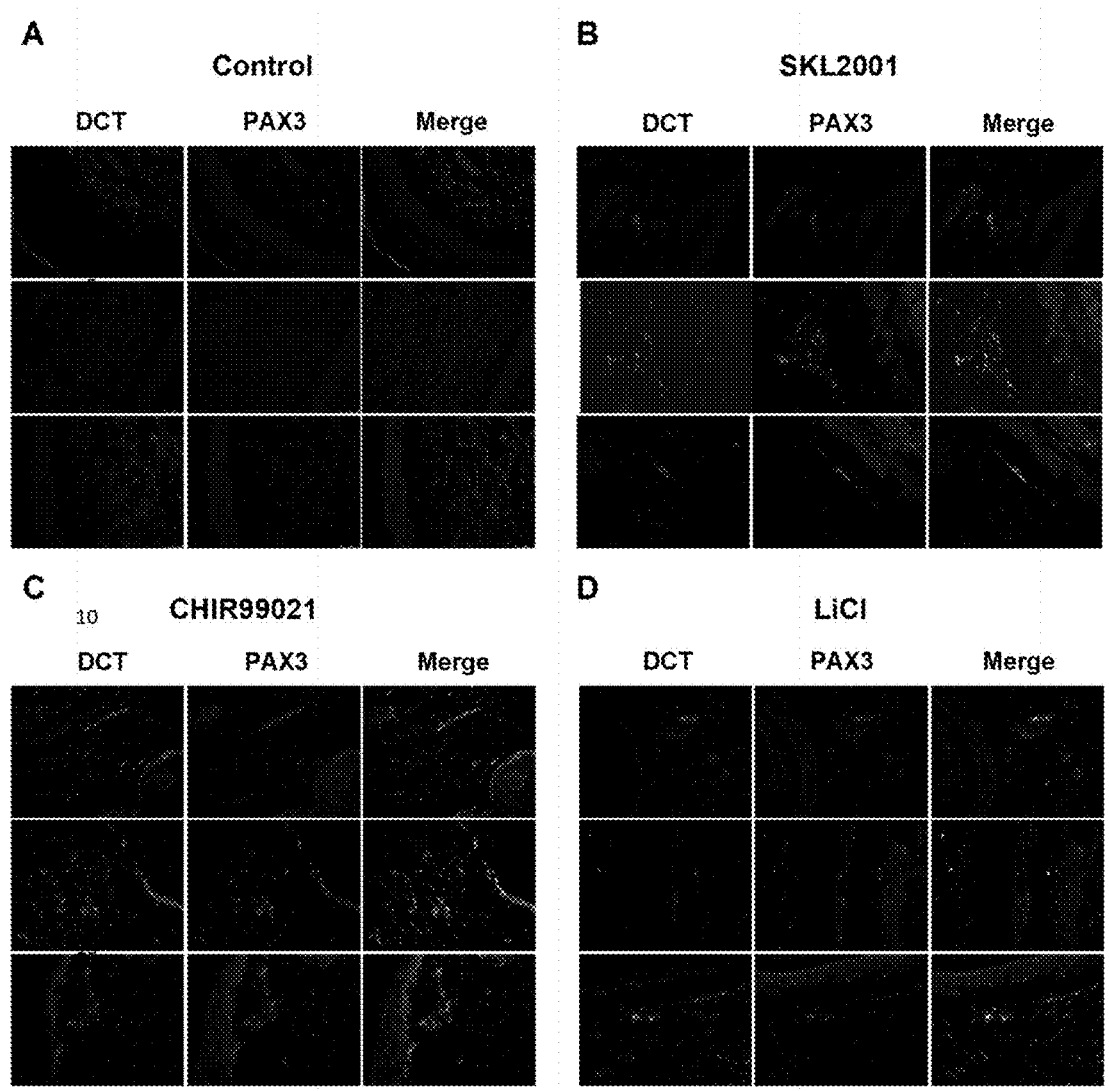

FIG. 7: Treatment of ex vivo depigmented skins from vitiligo patients with pharmacological WNT pathway activators induces the differentiation of resident stem cells into pre-melanocytes. Depigmented skin from vitiligo patients [A (control culture medium)] were stimulated in ex vivo culture with WNT agonist SKL2001 (40 μM) (B), GSK3β inhibitor CHIR99021 (3 μM) (C) or GSK3β inhibitor LiCl 20 μM (D) every other day to activate the WNT pathway. After 14 days, the skin response was analyzed by immunohistostaining with pre-melanocytes markers: a DCT staining (green) and PAX3 staining (red). The co localization (yellow) observed on merge pictures show melanoblast in differentiation within the dermis.

Figure 8:
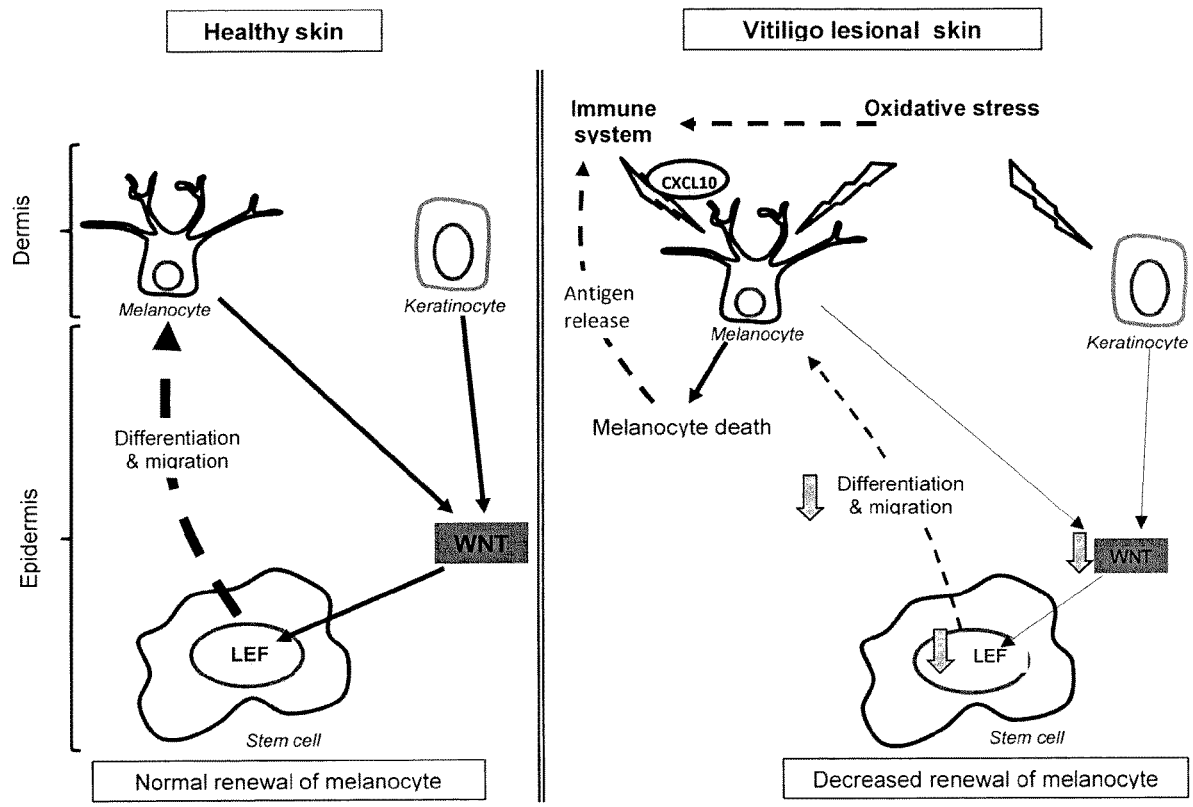

FIG. 8. Schematic representation of factors involved in vitiligo pathogenesis compared to healthy skin.

In healthy skin, the stimulation of the WNT pathway by keratinocytes and melanocytes induces the differentiation and the proliferation of melanocyte stem cells allowing the constant turnover of the pools of epidermal melanocytes. In vitiligo skin, the oxidative stress can trigger the immune reaction in a genetically predisposed subject. The destruction of the melanocytes by the immune system releases melanocyte antigens that stimulate the auto-immune response and ultimately lead to the complete disappearance of melanocyte from the epidermis (and sometimes the hair follicles). Concomitantly, the oxidative stress decreases the WNT pathway activity in melanocytes and in keratinocytes. This induces an altered differentiation of melanocyte stem cells and thus alters the capacity of melanocyte turnover. Depending on the patient and on the course of the disease, these two mechanisms are differentially implicated leading respectively to active depigmentation of the skin and resistance to repigmenting approaches.

FIG. 9:

(A) Schematic representation of skin sampling in vitiligo patient: Biopsies and Tape strippings were taken in lesional, perilesional and non lesional area. Matched samples were obtained from a similar body area from healthy volunteers.

(B) Characteristic of the studied population.

FIG. 10:

(A) NHM, (B) NHK and (C) whole skin in ex vivo culture were stimulated 24 hours with 25 to 100 μM of $H_2O_2$. After mRNA extraction, a reverse transcription was performed and the relative gene expression of WNT family was analyzed with qPCR.

FIG. 11:

Vitiligo patients (n=9) were biopsied in lesional skin area. The biopsies were stimulated in ex vivo culture during 14 days with GSK3β inhibitor: CHIR99021 (3 μM) or LiCl (20 μM) or with WNT agonist: SKL2001 (40 μM) every other day. mRNA was extracted and a RT-qPCR was performed to quantify the relative expression of WNT family.

EXPERIMENTAL PART

Vitiligo is an acquired depigmentation of the skin and sometimes hair follicle affecting 0.5% to 1% of the world's population. It is clearly demonstrated that vitiligo greatly impairs the quality of life of affected individuals and there is a strong therapeutic demand [Radtke, 2009] [Silverberg, 2013]. The pathophysiology is complex and involves many cellular players. There are strong evidences for a role of both oxidative stress and immune system in genetically predisposed individuals [Passeron, 2012] [Spritz, 2012; Jin, 2012] [Bellei, 2013] [Schallreuter, 2013]. One of the main problems studying vitiligo is that the affected cells, the melanocytes, are no longer present in the lesional skin. Moreover, increasing data emphasize the complexity of the pathophysiology of vitiligo with many cellular players involved such as keratinocytes, fibroblasts, stem cells, along with several types of immune cells. Thus, cell cultures can provide interesting information but they can't take into account the complex interactions occurring in vitiligo skin. Recently, animal models using reactive T-cells against melanocyte antigens provided very interesting data on the immune reaction potentially involved in the depigmentation of vitiligo skin but this model is not adapted to study mechanisms of melanocytes differentiation and repigmentation in vitiligo skin [Mosenson, 2013] [Rashighi, 2014]. To date, there is no definitive treatment for vitiligo.

Interestingly, in current practice man can frequently observe that some very active vitiligos can respond to treatment with a significant repigmentation while the surrounding skin continues to depigment. On the contrary, some patients with very stable vitiligo having no new depigmentation for years cannot achieve any repigmentation even using combined therapeutic approaches. This strongly suggests that some mechanisms are involved in depigmenting the skin (and to the light of the current data the immune system appears to play a key role in this process) while some others might be implicated to prevent or to inhibit the lesional vitiligo skin from repigmenting. This hypothesis is also supported by the marked difference in the response to treatment according to localizations. Indeed, hands, feet and face are the most common affected areas in vitiligo and they are also often together the firsts to depigment. However, although the face usually shows a high rate of response to treatment, hands and feet remain almost impossible to repigment [Ostovari, 2004; Passeron, 2004].

In order to characterize the pathophysiological mechanisms implicated in vitiligo human skin, inventors performed a transcriptome and proteomic analysis on lesional, perilesional and non-depigmented skin of vitiligo patients compared to matched skin controls of healthy subjects. When lesional vitiligo skins were compared to healthy controls, 152 genes were found to be upregulated and 181 down-regulated. Their results show that the immune reaction occurs at very low-level but confirm the potential role of CXCL10 for depigmenting vitiligo skin with a significant increase in non-depigmented and perilesional vitiligo skin compared to healthy controls. However, neither CXCL10 nor other immune factors were found to be deregulated in already depigmented vitiligo skin. Interestingly, the WNT pathway, implicated in melanocytes differentiation, was found to be altered in depigmented lesions but also in non-lesional skin. Inventors then showed in vitro that the oxidative stress decreases WNT expression/activation in keratinocytes and in melanocytes. They developed an ex vivo skin model that remains functional up to 15 days. They then confirmed the decreased activation of the WNT pathway in human skin subjected to oxidative stress. Finally, using pharmacological agents that activate the WNT pathway and pharmacological agents that inhibit GSK3B, they treated the ex vivo depigmented skins from vitiligo patients and success fully induced the differentiation of resident stem cells into pre-melanocytes. Their results shed light on the previously unrecognized role of a decreased WNT activation in depigmented vitiligo skin preventing melanocyte differentiation and they support further exploration of WNT agonists to repigment vitiligo lesions.

Material and Methods

Patients for Transcriptomic Analysis

Ten patients with active non segmental vitiligo, defined by the occurrence or the worsening of depigmented lesions in the past 3 months were included in the study after written consent was taken. The study was approved by the local ethical committee. A 4 mm diameter skin biopsy was taken for each patient in the center of a vitiligo patch, in the perilesional area (defined by 5 mm outside the border of the lesion) and in non-lesional skin located in the same area but at 3 cm minimum of a depigmented lesion. A 4 mm biopsy was also taken and served as control in 10 healthy patients matched for gender, age and localization. A scheme explaining how the samples were taken and the characteristic of the population are described in FIGS. 9A and 9B.

Transcriptomic Analysis

Quantification of Cytokines by Luminex in Stratum Corneum.

Stratum corneum was collected by tape stripping using Dsquames®, (Ø2.2 cm, D100, Monaderm, Monaco, France) as indicated in FIG. 9A. Proteins were extracted from non-lesional, lesional and perilesional stratum corneum in 2 ml Eppendorf tubes as follows: five Dsquames® were pooled and incubated in 200 µL ice-cold PBS containing Triton X100 0, 2% and protease inhibitors (complete, Mini, EDTA-free from Roche Applied Science, Mannheim, Germany) overnight at 4° C. under stirring at 1400 rpm in a thermo mixer (Eppendorf, Hanbourg Germany). To remove insoluble material, protein extracts were passed through 0.22 µm filters by centrifugation (Ultra free-MC PVDF, Millipore, Billerica, Mass.). Protein concentrations were determined using Dc Protein Assay (DC Kit, Bio-Rad Laboratories, Hercules, Calif.) and serum albumin as a standard. Extracts were kept at −80° C. until used. Cytokines were quantified in duplicate using following Luminex assays (Life Technologies, Carlsbad, Calif.): Human Cytokine, Premixed 62 Plex, ref PC1062M, Immunoassay Procarta kit from Affymetrix (Santa Clara, Calif., USA). Quality controls of all standard curves were performed. Cytokines were normalized to the total concentration of protein. All protein extracts with a concentration lower than 0.15 mg/ml of total protein, were not retained for the quantification of cytokines. Limits of quantification were calculated and considered for each protein. For cytokines with values below the limit of quantification, these values were not retained for normalization (i.e. calculation of cytokine levels in pg/mg of total protein). Fold changes were calculated and statistical analysis was performed using Array studio, T TEST linear model, False Discovery Rate: 0.05.

Cell Culture

NHMs and NHKs are obtained from the foreskin of phototype IV children as described previously. Briefly, epidermal cells are obtained by overnight digestion of the skin in a dispase solution (Roche) at 4° C. followed by the digestion of the epidermis in a trypsin/EDTA solution during 20 minutes at 37° C. NHMs are isolated in MCDB 153 medium (Sigma Aldrich) supplemented with 2% FBS (Perbio), 5 µg/ml insulin (Sigma Aldrich), 0.5 µg/ml hydrocortisone (Sigma Aldrich), 16 nM TPA (Sigma Aldrich), 1 ng/ml FGF (Promega), 15 µg/ml Bovine Pituitary Extract (Invitrogen), and 10 µM Forskolin (Sigma Aldrich) and 20 µg/ml geneticin (Invitrogen) during 2 weeks.

NHKs are isolated in KGM 2 medium (Promocell).

All cells are maintained at 37° C. in a 5% $CO_2$ atmosphere.

Ex Vivo Skin Culture

Skin from abdominoplasty surgery was used to the development of the ex vivo skin culture model. The subcutaneous fat was removed and biopsies of 6 mm were done in the skin composed of dermis and epidermis.

For vitiligo skin biopsies, after verification of the absence of melanocytes with Wood's lamp, two or three 6 mm biopsies composed of dermis plus epidermis were taken into lesional skin from vitiligo patients (n=9). The biopsies are rapidly put on transwell chamber of 0.4 µm (Becton Dickinson) and kept on semi liquid culture conditions in "Skin long term culture medium" (Biopredic). The skin was maintained at 37° C. in a wet 5% $CO_2$ atmosphere.

The culture medium supplemented with Forskolin (Sigma Aldrich), LiCl (Sigma Aldrich), CHIR99021 (Calbiochem) or SKL2001 (Calbiochem) was changed every days during 14 days.

mRNA Extraction and Analysis mRNA from melanocytes and keratinocytes was extracted with RNeasy kit (Qiagen). The biopsies are cut and disrupted with tissue ruptor (Qiagen) and the mRNA was extracted with RNeasy kit (Qiagen). cDNA were synthesized from 300 ng to 1 µg of mRNA with the Reverse Transcription System (Promega). Relative quantification of gene expression was measured by real time qPCR with Sybr green reagent (Life technology) on Step one system.

Infection of NHM and NHK and Luciferase Assay

NHK and NHM were co-infected with the lentivirus TCF/LEF Reporter Luciferase and Cignal Lenti Reporter Control Renilla (Qiagen) and the infected cells were selected with Puromycin for 14 days. NHM and NHK selected were stimulated 24 h with SKL2001 and $H_2O_2$ and the TCF/LEF activity was measured with Dual Luciferase Reporter Assay System (Promega).

Hematoxylin Eosin Staining

Biopsies are frozen in Tissu Tek OCT (Sakura), cut with cryostat in 7 µM section and disposed on superforst plus slides (Thermoscientific). Briefly, after fixation with Paraformaldehyde 4% (EMS), the slide was stained with Harry's Hematoxylin (Sigma Aldrich), rinse with chloride alcohol and carbonate Lithium (Sigma Aldrich) and stained with Erythrosine (Sigma Aldrich). After several rinses, the slides were dehydrated with ethanol and xylene and fixed with mounting medium.

Immunohistofluorescence

Biopsies were fixed with 4% formol, embedded in paraffin, cut with microtome of 7 µM sections and fixed on superfrost plus slides (Thermoscientific). After deparaffinization by successive xylene and ethanol incubations, the sections were hydrated with distilled water, permeabilized 10 minutes with 0.3% Triton and heated in microwave 12 minutes in citrate buffer (Vector Laboratory) to unmasking antigen. The sections were blocked 30 minutes in 10% goat serum and incubated in primary antibodies MITF (Abcam), Tyrosinase (αPEP7h), DCT (Novus) overnight at 4° C. After rinsing with PBS 0.05% Tween, the sections were incubated 1 hour with secondary antibodies Alexa 488 or Alexa 594 (Invitrogen) and Hoechst (Invitrogen). After rinsing, the slides were fixed with mounting medium.

Results

Figure 1C:
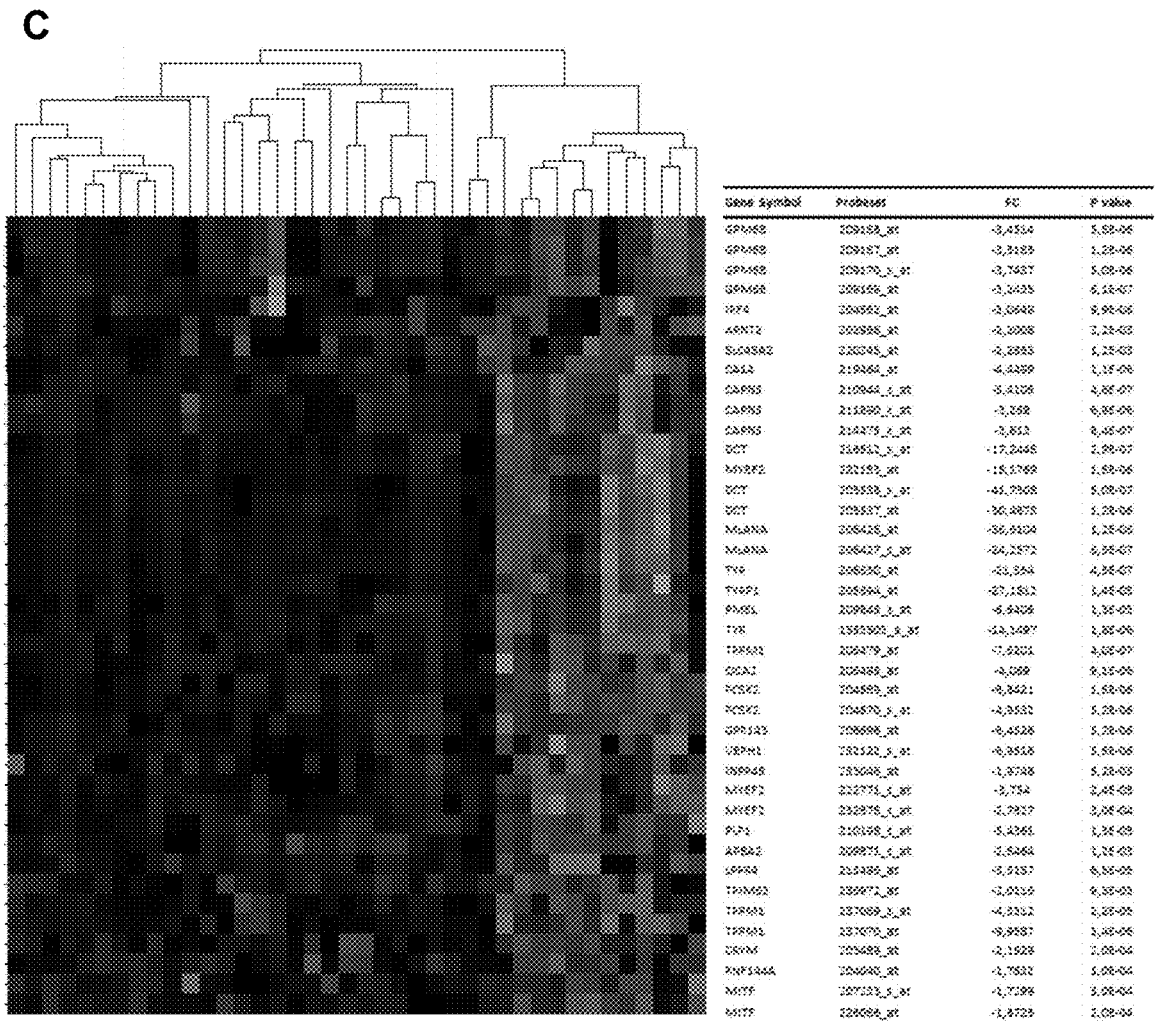

Transcriptome Analysis Shows that Immune Reaction Occurs Only at Low-Level and is Restricted to Non-Depigmented and Perilesional Vitiligo Skin and Reveals a Decreased Activation of the WNT Pathway Along with the Absence of Immune Reaction Signature in Already Depigmented Skin A total of 152 genes were found to be up-regulated and 181 down-regulated when lesional vitiligo skins were compared to healthy controls (FIG. 1A). When peri-lesional and non-depigmented vitiligo skins were compared to healthy controls, X, Y genes were found to be up-regulated and W, Z genes down-regulated, respectively. Interestingly, the ingenuity canonical pathway analysis revealed along with melanocyte development and pigmentation signaling that the circadian signaling and the WNT/beta-catenin pathway were significantly deregulated in vitiligo lesions compared to control (FIG. 1B). The cluster analysis of microarray data of the top genes from healthy skin (HS), non lesional (NLS), perilesional (PLS) and lesional skin (LS) from vitiligo subjects showed not surprisingly mostly melanocytic genes (FIG. 1C). Inventors specifically analyzed the expression of the genes related to the immune reaction. They observed very few variations among the several conditions and none reach the level of statistical significance (see Table 1).

Table 1

| Cell Pop | Probeset | Gene symbol | HS Mean_Expressions | NLS Mean_Expressions | LS Mean_Expressions | LS vs HS FC P-val | NLS vs HS FC P-val | PLS vs HS FC P-val | LS vs NLS FC P-val | PLS vs NLS FC P-val |
|---|---|---|---|---|---|---|---|---|---|---|
| B cells | 217281_x_at | IGH@ | 88 | 78 | 82 | 0.9 | 0.9 | 0.7 | 0.8 | 1.0 |
|  | 228518_at | IGHG1/IGHM | 70 | 64 | 67 | 0.6 | 0.3 | 0.6 | 0.5 | 0.9 |
|  | 216379_x_at | CD24 | 8189 | 7213 | 7343 | 0.4 | 0.4 | 0.3 | 0.8 | 1.0 |
|  | 205297_s_at | CD79B | 126 | 106 | 102 | 0.2 | 0.3 | 0.3 | 0.7 | 1.0 |
|  | 211693_at | IGHA1 | 135 | 125 | 133 | 0.9 | 0.4 | 1.0 | 0.4 | 0.9 |
|  | 223502_s_at | TNFSF13B | 265 | 296 | 240 | 0.7 | 0.7 | 0.9 | 0.2 | 0.9 |
| Langerhans cells | 210325_at | CD1A | 1096 | 1267 | 1354 | 0.2 | 0.5 | 0.5 | 0.5 | 1.0 |
|  | 211734_s_at | FCER1A | 2992 | 3198 | 3318 | 0.6 | 0.8 | 0.9 | 0.7 | 0.9 |
|  | 204232_at | FCER1G | 1480 | 1465 | 1492 | 1.0 | 1.0 | 0.8 | 0.9 | 0.9 |
|  | 207496_at | MS4A2 | 147 | 137 | 150 | 1.0 | 0.9 | 0.8 | 0.6 | 1.0 |
|  | 220428_at | CD207 | 629 | 713 | 739 | 0.5 | 0.7 | 0.8 | 0.8 | 0.9 |
| DermalDCs immature | 206749_at | CD1B | 56 | 103 | 70 | 0.7 | 0.2 | 0.5 | 0.2 | 0.9 |
|  | 205987_at | CD1C | 825 | 992 | 822 | 1.0 | 0.6 | 1.0 | 0.3 | 0.9 |
|  | 207277_at | CD209 | 792 | 926 | 821 | 0.9 | 0.7 | 0.9 | 0.6 | 0.9 |
|  | 210184_at | ITGAX | 106 | 112 | 93 | 0.6 | 0.9 | 0.6 | 0.2 | 0.9 |
|  | 205569_at | LAMP3 | 934 | 1324 | 1322 | 0.4 | 0.4 | 0.3 | 1.0 | 1.0 |
|  | 200785_s_at | LRP1 | 1377 | 1369 | 1195 | 0.6 | 1.0 | 0.6 | 0.3 | 0.9 |
|  | 205668_at | LY75 | 721 | 1026 | 983 | 0.1 | 0.1 | 0.2 | 0.7 | 0.9 |
|  | 204438_at | MRC1 | 3259 | 3029 | 2761 | 0.5 | 0.8 | 0.5 | 0.5 | 0.9 |
|  | 204924_at | TLR2 | 133 | 135 | 108 | 0.4 | 1.0 | 0.8 | 0.1 | 0.9 |
|  | 221060_s_at | TLR4 | 310 | 268 | 287 | 0.9 | 0.8 | 0.9 | 0.8 | 1.0 |
| DermalDCs activated | 205987_at | CD1C | 825 | 992 | 822 | 1.0 | 0.6 | 1.0 | 0.3 | 0.9 |
|  | 200784_s_at | LRP1 | 464 | 454 | 418 | 0.6 | 0.9 | 0.6 | 0.5 | 0.9 |
|  | 210325_at | CD1A | 1096 | 1267 | 1354 | 0.2 | 0.5 | 0.5 | 0.5 | 1.0 |
|  | 204440_at | CD83 | 366 | 452 | 428 | 0.6 | 0.5 | 0.6 | 0.7 | 0.9 |
|  | 205686_s_at | CD86 | 153 | 145 | 148 | 0.9 | 0.9 | 0.8 | 0.9 | 1.0 |
|  | 217028_at | CXCR4 | 3300 | 2857 | 2296 | 0.1 | 0.7 | 0.5 | 0.3 | 0.9 |
| pDCs | 206148_at | IL3RA | 130 | 118 | 114 | 0.3 | 0.5 | 0.2 | 0.7 | 0.9 |
| pDCs | 211734_s_at | FCER1A | 2992 | 3198 | 3318 | 0.6 | 0.8 | 0.9 | 0.7 | 0.9 |
|  | 204232_at | FCER1G | 1480 | 1465 | 1492 | 1.0 | 1.0 | 0.8 | 0.9 | 0.9 |
|  | 207496_at | MS4A2 | 147 | 137 | 150 | 1.0 | 0.9 | 0.8 | 0.6 | 1.0 |
|  | 203547_at | CD4 | 423 | 395 | 354 | 0.4 | 0.8 | 0.4 | 0.4 | 0.9 |
|  | 212298_at | NRP1 | 623 | 632 | 639 | 0.9 | 1.0 | 0.9 | 0.9 | 1.0 |
|  | 220146_at | TLR7 | 134 | 132 | 134 | 1.0 | 1.0 | 0.8 | 1.0 | 0.9 |
|  | 229560_at | TLR8 | 116 | 109 | 109 | 0.9 | 0.9 | 0.9 | 1.0 | 1.0 |
| IDECs | 204438_at | MRC1 | 3259 | 3029 | 2761 | 0.5 | 0.8 | 0.5 | 0.5 | 0.9 |
|  | 210325_at | CD1A | 1096 | 1267 | 1354 | 0.2 | 0.5 | 0.5 | 0.5 | 1.0 |
|  | 206749_at | CD1B | 56 | 103 | 70 | 0.7 | 0.2 | 0.5 | 0.2 | 0.9 |
|  | 205987_at | CD1C | 825 | 992 | 822 | 1.0 | 0.6 | 1.0 | 0.3 | 0.9 |
|  | 211734_s_at | FCER1A | 2992 | 3198 | 3318 | 0.6 | 0.8 | 0.9 | 0.7 | 0.9 |
|  | 204232_at | FCER1G | 1480 | 1465 | 1492 | 1.0 | 1.0 | 0.8 | 0.9 | 0.9 |
|  | 207496_at | MS4A2 | 147 | 137 | 150 | 1.0 | 0.9 | 0.8 | 0.6 | 1.0 |
|  | 205786_s_at | ITGAM | 460 | 421 | 446 | 1.0 | 0.9 | 1.0 | 0.8 | 0.9 |
|  | 242197_x_at | CD36 | 298 | 324 | 203 | 0.3 | 0.9 | 0.7 | 0.0 | 0.9 |
|  | 209555_s_at | CD36 | 1392 | 998 | 811 | 0.3 | 0.6 | 0.6 | 0.5 | 1.0 |
|  | 221463_at | CCL24 | 66 | 58 | 64 | 0.8 | 0.4 | 0.7 | 0.3 | 0.9 |
|  | 1555759_a_at | CCL5 | 225 | 236 | 219 | 1.0 | 0.9 | 0.9 | 0.8 | 1.0 |
|  | 211734_s_at | FCER1A | 2992 | 3198 | 3318 | 0.6 | 0.8 | 0.9 | 0.7 | 0.9 |
|  | 204232_at | FCER1G | 1480 | 1465 | 1492 | 1.0 | 1.0 | 0.8 | 0.9 | 0.9 |
|  | 207496_at | MS4A2 | 147 | 137 | 150 | 1.0 | 0.9 | 0.8 | 0.6 | 1.0 |
| Mastcells | 216474_x_at | TPSAB1/TPSB2 | 3027 | 3215 | 3397 | 0.8 | 0.9 | 1.0 | 0.8 | 0.9 |
|  | 214533_at | CMA1 | 665 | 608 | 725 | 0.8 | 0.9 | 0.9 | 0.3 | 1.0 |
|  | 205683_x_at | TPSAB1 | 3123 | 3329 | 3533 | 0.7 | 0.9 | 1.0 | 0.8 | 1.0 |
|  | 207134_x_at | TPSB2 | 2558 | 2743 | 2912 | 0.7 | 0.9 | 1.0 | 0.8 | 1.0 |
|  | 214568_at | TPSD1 | 74 | 72 | 77 | 0.7 | 0.9 | 1.0 | 0.4 | 0.9 |
|  | 220339_s_at | TPSG1 | 62 | 65 | 70 | 0.4 | 0.8 | 0.8 | 0.6 | 1.0 |
| Neutrophils | 206871_at | ELANE | 60 | 81 | 81 | 0.8 | 0.8 | 0.8 | 1.0 | 0.9 |
|  | 202018_s_at | LTF | 421 | 268 | 164 | 0.3 | 0.7 | 0.2 | 0.5 | 0.9 |
|  | 1555349_a_at | ITG82 | 284 | 295 | 254 | 0.7 | 0.9 | 0.8 | 0.3 | 0.9 |
| Macrophages | 201743_at | CD14 | 864 | 873 | 792 | 0.8 | 1.0 | 0.8 | 0.6 | 0.9 |
|  | 215049_x_at | CD163 | 1145 | 1398 | 1275 | 0.8 | 0.6 | 0.9 | 0.7 | 0.9 |
|  | 203507_at | CD68 | 96 | 72 | 78 | 0.6 | 0.4 | 0.4 | 0.4 | 1.0 |
|  | 205786_s_at | ITGAM | 460 | 421 | 446 | 1.0 | 0.9 | 1.0 | 0.8 | 0.9 |
|  | 202803_s_at | ITG62 | 504 | 543 | 448 | 0.7 | 0.9 | 0.8 | 0.2 | 0.9 |
| T cells | 217326_x_at | IL23A/TRBV19 | 93 | 91 | 92 | 0.9 | 0.8 | 0.2 | 0.9 | 0.9 |
|  | 216920_s_at | TARP/TRGC2 | 78 | 108 | 94 | 0.8 | 0.6 | 0.5 | 0.2 | 1.0 |
|  | 210972_x_at | TRAC/TRAJ17 | 653 | 644 | 541 | 0.5 | 1.0 | 0.9 | 0.2 | 0.9 |
|  | 206545_at | CD28 | 73 | 70 | 60 | 0.6 | 0.9 | 0.5 | 0.6 | 0.9 |
|  | 213539_at | CD3D | 338 | 398 | 322 | 0.9 | 0.7 | 1.0 | 0.3 | 0.9 |

Table 1-continued

| Cell Population | Probeset | Gene symbol | HS | NLS | LS | LS vs HS FC P-val | NLS vs HS FC P-val | PLS vs HS FC P-val | LS vs NLS FC P-val | PLS vs NLS FC P-val |
|---|---|---|---|---|---|---|---|---|---|---|
| | 206804_at | CD3G | 84 | 94 | 75 | 0.8 | 0.8 | 0.9 | 0.3 | 0.9 |
| | 203547_at | CD4 | 423 | 395 | 354 | 0.4 | 0.8 | 0.4 | 0.4 | 0.9 |
| | 205758_at | CD8A | 279 | 290 | 230 | 0.6 | 1.0 | 1.0 | 0.3 | 1.0 |
| | 236341_at | CTLA4 | 61 | 95 | 76 | 0.7 | 0.4 | 0.5 | 0.4 | 0.9 |
| | 214470_at | KLRB1 | 175 | 202 | 156 | 0.8 | 0.8 | 1.0 | 0.2 | 0.9 |
| | 209670_at | TRAC | 723 | 686 | 606 | 0.4 | 0.9 | 0.7 | 0.4 | 1.0 |
| | 211796_s_at | TRBC1 | 816 | 902 | 676 | 0.6 | 0.9 | 0.9 | 0.2 | 0.9 |
| | 216191_s_at | TRDV3 | 143 | 119 | 130 | 0.9 | 0.8 | 0.9 | 0.8 | 0.9 |
| | 211902_x_at | YME1L1 | 670 | 663 | 542 | 0.5 | 1.0 | 0.9 | 0.2 | 1.0 |
| Th1 | 206295_at | IL18 | 3261 | 2595 | 2983 | 0.7 | 0.2 | 0.4 | 0.1 | 0.9 |
| | AFFX-HUMISGF3A/M97935_M8_at | STAT1 | 220 | 305 | 276 | 0.5 | 0.3 | 0.2 | 0.7 | 0.9 |
| | AFFX-HUMISGF3A/M97935_3_at | STAT1 | 1655 | 1904 | 1751 | 0.9 | 0.6 | 0.5 | 0.6 | 1.0 |
| | 206118_at | STAT4 | 104 | 101 | 83 | 0.3 | 0.9 | 0.3 | 0.3 | 0.9 |

| Cell Population | Probeset | Gene symbol | HS | NLS | LS | LS vs HS FC P-val | NLS vs HS FC P-val | PLS vs HS FC P-val | LS vs NLS FC P-val | PLS vs NLS FC P-val |
|---|---|---|---|---|---|---|---|---|---|---|
| | 207113_s_at | TNF | 86 | 115 | 110 | 0.2 | 0.1 | 0.4 | 0.8 | 0.9 |
| Th17 | 206890_at | IL12RB1 | 63 | 59 | 66 | 0.7 | 0.5 | 0.9 | 0.1 | 0.9 |
| | 203085_s_at | TGFB1 | 163 | 170 | 175 | 0.8 | 0.9 | 1.0 | 0.8 | 0.9 |
| | 208991_at | STAT3 | 4197 | 4454 | 4173 | 1.0 | 0.7 | 0.7 | 0.3 | 1.0 |
| | 225289_at | STAT3 | 932 | 947 | 973 | 0.9 | 1.0 | 0.7 | 0.8 | 0.9 |
| | 228806_at | RORC | 232 | 289 | 271 | 0.3 | 0.2 | 0.2 | 0.4 | 1.0 |
| | 207113_s_at | TNF | 86 | 115 | 110 | 0.2 | 0.1 | 0.4 | 0.8 | 0.9 |
| | 206983_at | CCR6 | 516 | 468 | 475 | 0.7 | 0.7 | 0.7 | 0.9 | 1.0 |
| Th2 | 201331_s_at | STAT6 | 3645 | 2756 | 2886 | 0.1 | 0.1 | 0.1 | 0.6 | 1.0 |
| | 203233_at | IL4R | 562 | 585 | 510 | 0.8 | 0.9 | 0.6 | 0.4 | 0.9 |
| Treg | 224211_at | FOXP3 | 78 | 82 | 79 | 0.9 | 0.8 | 0.8 | 0.7 | 1.0 |
| Chemokines | 205392_s_at | CCL14/CCL14– | 3178 | 2449 | 2232 | 0.2 | 0.5 | 0.2 | 0.4 | 0.9 |
| | 205114_s_at | CCL15/CCL15/CCL3/CCL3L1/CCL3L3/ | 75 | 67 | 68 | 0.8 | 0.9 | 0.8 | 1.0 | 1.0 |
| | 206407_s_at | CCL13 | 1899 | 3519 | 2504 | 0.4 | 0.04 | 0.3 | 0.2 | 0.9 |
| | 32128_at | CCL18 | 565 | 1512 | 922 | 0.50 | 0.1 | 0.4 | 0.2 | 0.9 |
| | 210072_at | CCL19 | 588 | 664 | 459 | 0.6 | 0.9 | 0.7 | 0.2 | 0.9 |
| | 216598_s_at | CCL2 | 878 | 1016 | 957 | 0.9 | 0.8 | 1.0 | 0.8 | 0.9 |
| | 204606_at | CCL21 | 1895 | 1989 | 1773 | 0.9 | 0.9 | 1.0 | 0.4 | 0.9 |
| | 207861_at | CCL22 | 430 | 584 | 538 | 0.6 | 0.4 | 0.6 | 0.7 | 0.9 |
| | 210549_s_at | CCL23 | 133 | 103 | 113 | 0.8 | 0.7 | 0.7 | 0.4 | 0.9 |
| | 207955_at | CCL27 | 3493 | 4217 | 3880 | 0.9 | 0.8 | 0.9 | 0.7 | 0.9 |
| | 1555759_a_at | CCL5 | 225 | 236 | 219 | 1.0 | 0.9 | 0.9 | 0.8 | 1.0 |
| | 214038_at | CCL8 | 292 | 382 | 249 | 0.8 | 0.7 | 1.0 | 0.3 | 0.9 |
| | 203915_at | CXCL9 | 94 | 163 | 189 | 0.6 | 0.8 | 0.6 | 0.9 | 1.0 |
| | 823_at | CX3CL1 | 213 | 249 | 212 | 1.0 | 0.7 | 0.9 | 0.4 | 0.9 |
| | 206366_x_at | XCL1 | 87 | 93 | 100 | 0.7 | 0.9 | 0.7 | 0.8 | 0.9 |
| Chemokine receptors | 205098_at | CCR1 | 143 | 147 | 151 | 0.9 | 1.0 | 1.0 | 0.9 | 1.0 |
| | 206978_at | CCR2 | 178 | 187 | 159 | 0.8 | 0.9 | 0.8 | 0.5 | 0.9 |
| | 211286_x_at | CSF2RA | 112 | 109 | 110 | 0.9 | 0.9 | 0.7 | 0.9 | 0.9 |
| | 205159_at | CSF2RB | 530 | 709 | 651 | 0.3 | 0.1 | 0.2 | 0.5 | 1.0 |
| | 205898_at | CX3CR1 | 277 | 278 | 266 | 0.9 | 1.0 | 0.9 | 0.8 | 0.9 |
| | 207008_at | CXCR2 | 170 | 130 | 148 | 0.7 | 0.4 | 0.4 | 0.5 | 1.0 |
| | 217028_at | CXCR4 | 3300 | 2857 | 2296 | 0.1 | 0.7 | 0.5 | 0.3 | 0.9 |
| Cytokines | 205992_s_at | IL15 | 104 | 142 | 126 | 0.6 | 0.4 | 0.5 | 0.5 | 0.9 |
| | 227401_at | IL17D | 450 | 507 | 443 | 1.0 | 0.8 | 0.8 | 0.4 | 0.9 |
| | 203828_s_at | IL32 | 768 | 783 | 630 | 0.6 | 1.0 | 0.7 | 0.2 | 0.9 |
| | 209821_at | IL33 | 1310 | 940 | 928 | 0.1 | 0.2 | 0.1 | 0.9 | 0.9 |
| | 224555_x_at | IL37 | 4909 | 4131 | 4379 | 0.6 | 0.5 | 0.7 | 0.6 | 0.9 |
| | 231755_at | IL36B | 134 | 81 | 105 | 0.5 | 0.1 | 0.3 | 0.1 | 0.9 |
| | 220322_at | IL36G | 543 | 460 | 690 | 0.6 | 0.8 | 1.0 | 0.1 | 0.9 |
| | 222223_s_at | IL36RN | 3045 | 2873 | 3793 | 0.3 | 0.9 | 0.8 | 0.0 | 0.9 |
| | 206693_at | IL7 | 177 | 171 | 212 | 0.4 | 0.9 | 0.7 | 0.0 | 0.9 |
| | 212195_at | IL6ST | 3950 | 3922 | 3728 | 0.6 | 1.0 | 0.7 | 0.4 | 0.9 |
| | 207339_s_at | LTB | 171 | 225 | 188 | 0.8 | 0.3 | 0.7 | 0.3 | 0.9 |
| | 223501_at | TNFSF13B | 144 | 159 | 144 | 1.0 | 0.7 | 1.0 | 0.5 | 0.9 |
| Cytokine receptors | 202727_s_at | IFNGR1 | 3317 | 3291 | 3211 | 0.8 | 1.0 | 0.7 | 0.7 | 0.9 |
| | 1552584_at | IL12RB1 | 225 | 267 | 253 | 0.8 | 0.7 | 0.7 | 0.9 | 1.0 |
| | 201887_at | IL13RA1 | 1440 | 1598 | 1433 | 1.0 | 0.6 | 0.8 | 0.3 | 0.9 |
| | 207375_s_at | IL15RA | 267 | 274 | 259 | 0.9 | 1.0 | 0.8 | 0.7 | 0.9 |
| | 219115_s_at | IL20RA | 732 | 812 | 867 | 0.5 | 0.7 | 0.5 | 0.6 | 0.9 |
| | 205926_at | IL27RA | 88 | 83 | 71 | 0.4 | 0.9 | 0.5 | 0.3 | 0.9 |
| | 205291_at | IL2RB | 223 | 161 | 162 | 0.2 | 0.3 | 0.3 | 1.0 | 1.0 |
| | 204116_at | IL2RG | 410 | 453 | 383 | 0.9 | 0.9 | 1.0 | 0.3 | 0.9 |
| | 203233_at | IL4R | 562 | 585 | 510 | 0.8 | 0.9 | 0.6 | 0.4 | 0.9 |
| | 226218_at | IL7R | 550 | 458 | 327 | 0.2 | 0.8 | 0.5 | 0.1 | 0.9 |
| | 226621_at | OSMR | 1317 | 1370 | 1332 | 1.0 | 0.9 | 1.0 | 0.7 | 0.9 |

Interestingly, a transcriptional network linking WNT signaling and melanogenesis pathways was observed using inguinity analysis pathways (FIG. 2). Lesional vitiligo skin is both characterized by a down-regulated expression of key transducer of WNT signaling pathway (E.g. LEF1), and by the upregulation of negative regulators of WNT signaling pathway DVL1 and p53 (involved in signal transduction of WNT members) and TLE4 (groucho family member) and ZBTB33/Kaiso (involved in transcriptional repression of WNT target genes).

The circadian genes were found to be modulated in our transcriptional analysis. Due to the demonstrated role of the variation of these genes during the day, inventors investigate if this modulation was due to the time when the skin samples were biopsied or was linked to vitiligo pathogenesis. They thus analyzed the expression of the key circadian genes (ARNTL (Bmal1), CLOCK, PER1, NR1D1) accordingly to the hour of the samples were taken. A strong correlation between the hours of the samples and the expression of all these genes was found, showing that the modulation of the circadian gene expression was not linked to the vitiligo but to the moment where the samples were taken. The results of the transcriptional analysis were then controlled using TLDA. The marked decrease in all the melanocytic genes in vitiligo skin compared to control confirms the loss of melanocytes in the affected vitiligo skin (FIG. 3A). Inventors then analyzed the level of expression of LEF1 as a key marker of the activation of the WNT pathway. Conformingly with the results of the transcriptional analysis, the expression of LEF1 was found to be down-regulated in lesional vitiligo skin (FIG. 3B). As an additional control and to investigate if the expression of LEF1 could be modulated by the circadian cycle, they synchronized melanocytes and followed the relative expression of ARNTL and LEF1. The results showed that the expression of LEF1 is not correlated with the expression of ANRTL, a marker of circadian cycle. They reproduced this experiment following the expression of several WNT mRNA during the circadian cycle and observed no correlation (data not shown). Thus, the modulations of the WNT pathway observed in the transcriptome and TLDA analyses are linked to the pathogenesis of vitiligo. Finally, taking into account the results that suggested in mice model of vitiligo the role of CXCL10, they also analyzed its expression in the skin samples by TLDA. Interestingly, they observed a significant increase in mRNA expression of CXCL10 in perilesional skin but also in non-depigmented skin of vitiligo patients compared to healthy controls. However, the level of expression of CXCL10 was not different from healthy skin in depigmented vitiligo lesions (FIG. 3C).

Taken together, these results obtained from vitiligo patients compared to healthy subjects do not show significant modulation of genes involved in the immune reaction except for CXCL10 that was found to be up-regulated in peri-lesional but also non-depigmented skin of vitiligo patients. They also show that no more immune reaction is observable in lesional skin devoid of melanocytes. Interestingly, they mostly reveal a down-regulation of the WNT/beta-catenin pathway in vitiligo skin.

Analysis of Stratum Corneum Cytokines Shows No Significant Dysregulation in Vitiligo Skin The concentrations of 62 cytokines were measured in stratum corneum of subject with vitiligo and healthy volunteers using tape stripping a minimal invasive method. Twelve cytokines were detected and quantified from stratum corneum extracts with a concentration ranging from 1 to 7000 pg/mg of protein (see below Table 2).

TABLE 2

Quantity of cytokines in stratum corneum

| cytokines | Healthy | Lesional | Non-lesional | Peri-lesional |
|---|---|---|---|---|
| IL-1RA (IL1R1) | 5626 | 7012 | 3201 | 7058 |
| IL-1alpha (IL-1F1) | 2245 | 3165 | 3242 | 3499 |
| G-CSF (CSF-3) | 1987 | 1812 | 995 | 1850 |
| EGF | 37 | 17 | 9 | 9 |
| CXCL10 (IP-10) | 23 | 38 | 34 | 35 |
| CXCL9 (MIG) | 19 | 26 | 24 | 24 |
| IL-1Beta (IL-1F2) | 15 | 30 | 8 | 30 |
| sICAM-1 (CD54) | 12 | 14 | 10 | 10 |
| sVCAM-1 (CD106) | 8 | 7 | 5 | 6 |
| CCL11 (EOTAXIN) | 7 | 8 | 7 | 7 |
| CXCL1 (GROalpha) | 6 | 6 | 6 | 6 |
| CCL2 (MCP-1) | 5 | 5 | 4 | 4 |

Quantity (pg/mg) of cytokine in stratum corneum (mean-normalized values). sFAS TNFRSF6, GM-CSF CSF-2, MCP-3 CCL7, IL-15, TNF-alpha, sE-Selectin CD62E ELAM1, MPO Myeloperoxidase, VEGF-A, IL-22 IL-TIF, MIP1-Beta CCL4, IL-3, IL-27, IL-4, ENA-78 CXCL5, SDF-1 CXCL12, Trail TNFSF10, IL-5, IL-20, FRAC-TALKINE CX3CL1, GRANZYME B, IFNomega IFNW1, IL-8 CXCL8, MIP-3alpha CCL20, IL-10 CSIF, IFNalpha2, BLC CXCL13 BCA-1, IL-7, PDGFBB, I-TAC CXCL11, IL-17F ML-1, IL-17A CTLA8, IL-6, sCD40-Ligand TNFSF5 CD40LG, TNF-Beta TNFSF1 LTA, IL-13, IL-23 p19, IFNg, IL-12 p'70, IL-21, IL-2, IL-9, TNFRI TNFRSF1A, TNFR II TNFRSF1B, RANTES CCL5, TGFalpha, IL-2RA CD25, IFNbeta, FGF BASIC, IL-12 IL-23 p40, MIP-1 alpha CCL3 were found under limit of quantification.

No significant difference in cytokine profile between pathological and non-pathological samples was observed (Table 3).

Table 3: Fold change lesional, peri-lesional and non-lesional versus healthy. No significant modulation was observed. In addition, no significant modulation was found for the following comparison: lesional versus non-lesional, lesional versus peri-lesional and peri-lesional versus non-lesional (data not shown).

| cytokines | Lesional versus healthy | Pval | Peri-lesional versus Healthy | Pval | Non-lesional versus Healthy | Pval |
|---|---|---|---|---|---|---|
| IL-1Beta (IL-1F2) | 2.1 | >0.05 | 2.1 | >0.05 | -1.8 | >0.05 |
| CXCL10 (IP-10) | 1.6 | >0.05 | 1.5 | >0.05 | 1.5 | >0.05 |
| IL-1alph a (IL-1F1) | 1.4 | >0.05 | 1.6 | >0.05 | 1.4 | >0.05 |
| CXCL9 (MIG) | 1.4 | >0.05 | 1.3 | >0.05 | 1.3 | >0.05 |
| IL-1RA IL1R1 | 1.2 | >0.05 | 1.3 | >0.05 | -1.8 | >0.05 |
| sICAM-1 (CD54) | 1.2 | >0.05 | -1.1 | >0.05 | -1.1 | >0.05 |
| CCL11 (EOTAXIN) | 1.1 | >0.05 | -1 | >0.05 | -1 | >0.05 |
| CXCL1 (GROalpha) | 1 | >0.05 | -1.1 | >0.05 | -1.1 | >0.05 |
| CCL2 (MCP-1) | -1 | >0.05 | -1.1 | >0.05 | -1.1 | >0.05 |
| G-CSF (CSF-3) | -1.1 | >0.05 | -1.1 | >0.05 | -2 | >0.05 |
| sVCAM-1 (CD106) | -1.2 | >0.05 | -1.3 | >0.05 | -1.6 | >0.05 |
| EGF | -2.1 | >0.05 | -3.9 | >0.05 | -4.1 | >0.05 |

The concentration of CXCL10 protein in the stratum corneum was compared to the mRNA expression obtained with the skin biopsies. While CXCL10 was found to be significantly up-regulated within the non lesional and peri lesional vitiligo skins compared to controls at the mRNA level, no significant modulation was observed at the protein level in the stratum corneum (see below Table 4).

Table 4: Comparison at mRNA and protein level of the expression of CXCL10 in all subjects

| CXCL10 (IP-10) | Lesional versus healthy | Pval | Peri-lesional versus Healthy | Pval | Non-lesional versus Healthy | Pval |
|---|---|---|---|---|---|---|
| mRNA (TLDA) | 1.25 | >0.05 | 4.6 | 0.04 | 4.5 | 0.03 |
| Protein (Luminex) | 1.6 | >0.05 | 1.5 | >0.05 | 1.5 | >0.05 |

These results show that the immune reaction in vitiligo occurs at very low-level.

Oxidative Stress Decreases WNT Pathway in the Skin

Since the WNT pathway, implicated in melanocytes differentiation, seems to be affected in vitiligo skin, inventors tried to determine the element—known to be involved in vitiligo—responsible for this dysregulation. Oxidative stress was reported to inhibit the WNT/beta-catenin pathway in kidney cells [Shin, 2004]. Inventors studied the impact of oxidative stress on WNT/beta-catenin activation within the skin. They induced an oxidative stress with $H_2O_2$ in melanocytes and keratinocytes and analyzed the expression of LEF and WNT family. After 24 hours in presence of $H_2O_2$, the expression of LEF and of the majority of WNT was decreased both in melanocytes (FIG. 4A and FIG. 10A) and keratinocytes (FIG. 4B and FIG. 10B). The same result was observed in whole skin as the stimulation of skin biopsies in an ex-vivo model (validated in FIG. 4) with $H_2O_2$ induced a decrease expression of LEF and of most of the WNT family (FIG. 4C and FIG. 10C).

Finally, inventors studied the LEF promoter activity under oxidative stress. They used a TCF/LEF luciferase reporter in melanocytes and keratinocytes. Concordantly to the decrease expression of several WNT under oxidative stress, the activity of the TCF/LEF promoter was also decreased in a dose responsive manner under oxidative stress.

Taken together these results show that the oxidative stress maintains a low activation of the WNT/beta-catenin pathway.

Development of an Ex Vivo Model to Study Vitiligo Skin

The difficulty to study vitiligo disease is due in particular to the absence of model that mimics the in vivo conditions and also contains stem cells that could be targeted to induce repigmentation. Inventors developed an ex vivo skin model viable for a period long enough to allow induction of the differentiation of melanocyte stem cells in vitiligo skin. In clinical practice vitiligo lesions usually take months to achieve repigmentation (if any). However, in best cases, the onset of pigmentation can sometimes be observed after 15 days of treatment. Inventor's objective was to obtain a skin morphologically correct and able to respond to a pigmentation inducer, such as forskolin, after 15 days of culture ex vivo. From abdominoplasty skin surgery, inventors determine the conditions required to satisfy these conditions. They used 6 mm biopsies composed of dermis and epidermis, disposed on transwell chamber in order to put the skin in semi liquid culture conditions. After 15 days in ex vivo culture, the morphology of the skin was considered acceptable. They noted only a decrease of dermal papillae compared to initial conditions that could be due to a difference of tension in the skin (FIG. 5A). The capacity of the skin to responds to forskolin was then analyzed by qPCR and immunohistofluorescence by studying the expression of the melanogenic genes MITF, DCT and tyrosinase. A dose response of forskolin was performed with one stimulation of forskolin in systemic conditions every other day. As expected, the first response was the up-regulation of MITF mRNA (FIG. 5B) and protein (FIG. 5C) after 11 days of stimulation. This phenomenon is transient but a high expression persists after 15 days at low forskolin concentration (FIG. 5B). At 15 days, they observed a strong increase at mRNA and protein level of the melanogenic enzymes DCT and tyrosinase (FIGS. 5B and 5C). To conclude, inventors obtained a model of ex vivo skin culture viable and functional until 15 days of culture.

Pharmacological WNT Pathway Activators Induce an Increase of WNT Expression in Ex Vivo Vitiligo Skin.

WNT pathway is implicated in melanocyte differentiation and inventors showed that it is altered in vitiligo skin. In order to induce the differentiation of melanocyte stem cells, they pharmacologically activated the WNT pathway in vitiligo skin cultured ex vivo as shown previously. They used two methods to activate the WNT pathway: a WNT agonist (SKL2001) and two GSK3β inhibitors: lithium chloride (LiCl) and a commercial specific inhibitor (CHIR99021). They biopsied 9 vitiligo subjects (6 mm punch) on diverse body locations (4 on elbow, 2 on trunk, 2 on leg, 1 on arm and 1 on axilla) and treated the ex vivo culture model during 14 days with a systemic stimulation every other day with the WNT activators.

Figure 11:
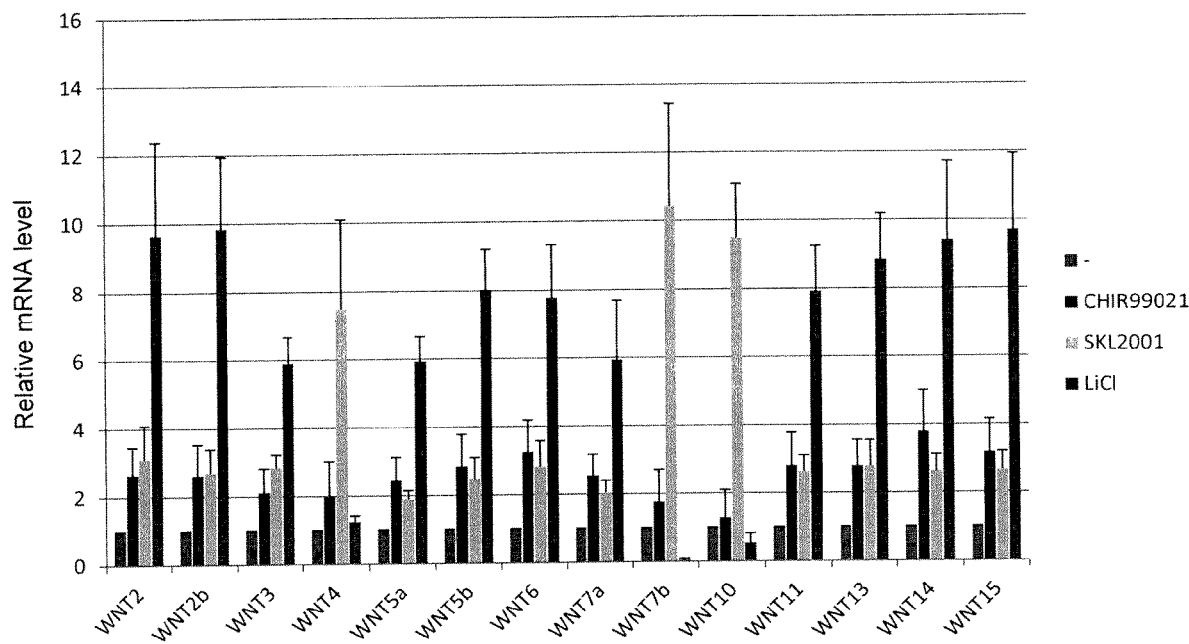

They evaluated the activation of WNT pathway by the mRNA level of WNTs (TCF/LEF1 and the melanogenesis pathway by the mRNA level of MITF, DCT, PAX3 and BRn2) within the skin. Treatments with LiCl, CHIR99021 and SKL2001 induce an increase of all WNT and LEF after 14 days of stimulation (FIG. 6A and FIG. 11). In their model the LiCl was particularly efficient to up-regulate WNT expression.

Treatment of Ex Vivo Depigmented Skins from Vitiligo Patients Induces the Differentiation of Resident Stem Cells into Pre-Melanocytes.

Since inventors succeeded to increase the WNT pathway in the ex vivo vitiligo skins, they analyzed the expression of melanoblast markers under treatment. The mRNA level of early melanoblast markers as PAX3 and Brn2 were up-regulated in biopsies stimulated with CHIR99021, SKL2001 and LiCl (FIGS. 6B and 6C). This result suggests an initiation of melanocytes differentiation. The level of MITF was increased only in skin treated with SKL2001 but its expression is transient after stimulation so they supposed that the time response was different between the treatments (FIG. 6D). The pre-melanocyte marker DCT was increased in response to all treatments but the effect was stronger in response to LiCl (FIG. 6E).

As they observed the up-regulation of mRNA level of melanoblast markers in the skin treated with WNT pathway activators, they investigated if these treatments have allowed the differentiation of melanocytes stem cells in pre-melanocytes in the skin by studying the co-expression of DCT and PAX3 by immunofluorescence. In vitiligo skins cultured in control conditions, they observe no or few isolated cells expressing PAX3 and DCT (FIG. 7A). In stimulated conditions (FIGS. 7B, 7C, 7D), inventors found, in the dermis and in the hair follicles, many group of cells expressing the two markers representing the melanocytes in differentiation. Taken together these results showed that targeting the deficient WNT pathway of vitiligo skin by using WNT agonists or GSK3B inhibitors allows the differentiation of melanocyte stem cells into pre-melanocytes.

Discussion

Inventors' results emphasize the complexity of vitiligo pathophysiology. While they support the role of the immune system and especially CXCL10 for depigmenting the skin of vitiligo patients, they also show that neither CXCL10 nor other immune factors are deregulated in already depigmented vitiligo skin. Recently, the role of CXCL10 and the IFNγ pathway was demonstrated in vitiligo mice model [Harris, 2012] [Rashighi, 2014]. The increased expression of CXCL10 was also found to be up-regulated in vitiligo skin. Interestingly, the skin samples analyzed were selected to still have an immune infiltrate [Rashighi, 2014]. Inventor's results are consistent with these data as they show an increase in CXCL10 expression in perilesional skin when compared to the CXCL10 expression in healthy control. However they also discovered that CXCL10 expression is significantly increased within unaffected skin of vitiligo patients when compared to healthy control skin, suggesting that even non-depigmented skin in vitiligo patients has low-level immune activation that culminates in CXCL10 expression. On the contrary, they do not observed an increased expression of CXCL10 in depigmented lesions that lack melanocytes, suggesting that the low-level immune activation in vitiligo skin is dependent on melanocytes. Other data support the fact that the immune reaction in vitiligo is restricted to differentiated melanocytes [Mosenson, 2013] [Chatterjee, 2014]. The only other transcriptome analysis performed in vitiligo skin did not show a potent activation of the immune system and only reported an activation of some factors involved in the innate immunity (in particular on natural killer cells) that inventors couldn't find in their analysis [Yu, 2012]. This first transcriptome study was performed in unaffected skin and lesional depigmented areas and compared to matched control. Interestingly, the authors found also an activation of natural killer cells in the unaffected vitiligo skin supporting a low-level immune activation in non-depigmented skin. They additionally performed a proteomic analysis of stratum corneum cytokines. The levels of cytokines in stratum corneum using immunoassays had never been performed before in vitiligo skin but they were investigated in several skin diseases including for example psoriasis [Gearing, 1990] and atopic dermatitis [Kezic, 2012] and also in skins exposed to UVB [Janssens, 2009] or chemical agent such as sodium lauryl sulphate [de Jongh, 2007]. Inventors found no significant modulation of cytokines between lesional, perilesional and unaffected vitiligo skin when compared to control. This is probably explained by the low-grade inflammation process occurring in vitiligo as compared to other dermatitis such as psoriasis or atopic dermatitis. Interestingly, inventors recently showed in a prospective randomized placebo controlled study that twice weekly application of 0.1% tacrolimus ointment significantly decreases the relapse rate of vitiligo lesions that were successfully repigmented (Cavalié, J Invest Derm in Press). The efficacy of this maintenance therapy, previously also shown in atopic dermatitis [Schmitt, 2011], strongly suggests in accordance to the data gathered in the present transcriptional study, that a low-level immune reaction occurred in pigmented skin of vitiligo patients. To summarize, these data demonstrate in Human skin the role of an immune reaction restricted to differentiate melanocytes and occurring at low-level in active vitiligo lesions but also in non-depigmented vitiligo skin with a central role of CXCL10. On the contrary, the immune reaction is no longer present in vitiligo lesions devoid of differentiated melanocytes.

Though, some depigmented vitiligo lesions will rapidly respond to treatment when other should resist to all the current approaches including phototherapy. Phototherapy is one of the key treatments against vitiligo [Taieb, 2013]. Its mechanism of action on vitiligo is still poorly understood but more than its action on the immune reaction, phototherapy is mainly active through the stimulation of the differentiation of melanocyte stem cells. Interestingly, recent data showed that the WNT/beta-catenin pathway is playing a key role in the UVB induced melanocyte stem cell differentiation [Yamada, 2013]. Within the skin, the secretion of WNT principally by keratinocytes contributes to the differentiation of stem cells in melanocytes. Inventors' transcriptional analysis reveals an alteration of the WNT/beta-catenin pathway in vitiligo skin with a significant decrease of LEF/TCF expression that was confirmed using TLDA. They additionally showed that oxidative stress inhibits the WNT/beta catenin activation in melanocytes and in keratinocytes. They confirmed this action on ex vivo skin models. Recently, a first link was discovered connecting oxidative stress and activation of the immune response [Toosi, 2012] [Passeron, 2012]. Our data underline that the oxidative stress has also a negative impact on the differentiation of melanocyte stem cells by inhibiting the WNT/beta-catenin pathway. Interestingly, several studies reported a beneficial role of oral or topical antioxidants for treating vitiligo [Schallreuter, 1995] [Dell'Anna, 2007] [Schallreuter, 2013]. However, there are some conflicting results on the efficacy of antioxidants for treating vitiligo [Bakis-Petsoglou, 2009]. Thus, inventors further decided to directly address the defective differentiation of melanocyte stem cells by stimulating the WNT/beta-catenin pathway that they demonstrated to be inhibited in vitiligo lesions. To this respect they developed an ex vivo skin model that they show to be advantageously viable and functional to up to 15 days. Using this ex vivo model in depigmented skins of vitiligo patients they demonstrated that treatments with WNT agonists or GSK3B inhibitors induce a strong increase of melanocyte markers. Ultimately, they showed that such treatments induce the differentiation of resident melanocyte stem cells in pre-melanocytes expressing PAX3 and DCT. Interestingly, they observed pre-melanocytes in the hair-follicles but also in the dermis suggesting that this approach could be helpful to differentiate the dermal stem cells of glabrous skin that are usually not effectively stimulated by phototherapy as a perifollicular pigmentation is observed in most cases. This allows a repigmentation of usually resistant areas such as hand or foot glabrous skin. Our results show the usefulness of ex vivo model of vitiligo skins for studying mechanisms involved in the differentiation of melanocytes but also for testing new treatments. Beyond the development of a new model for studying vitiligo, these results emphasize the interest of activating the WNT/beta-catenin pathway for inducing differentiation of melanocyte stem cells and thus a repigmentation in vitiligo lesions. The previously unrecognized implication of a decreased WNT/beta-catenin activation in vitiligo lesions brings new clues for understanding the discrepancy between therapeutic responses between localizations such as face compared to hands or feet. Indeed fibroblast-secreted factors, such as DKK1, decrease pigmentation on palms and soles by inhibiting the WNT/beta-catenin pathway [Yamaguchi, 2008; Yamaguchi, 2007]. Increasing evidences show that dermal fibroblast characteristics define regional differences in skin [Thangapazham, 2014]. To the light of our data, it can be hypothesized that regional factors decreasing the WNT-beta-catenin pathway, such as DKK1, further inhibit the already defective activation of this pathway in vitiligo skin and thus prevent repigmentation in these areas. The use of topical WNT agonist agents thus represent a powerful approach for inducing repigmentation in vitiligo skin that might be also effective in difficult to treat areas such as hands and feet. For repigmenting vitiligo lesions, a topical approach would be sufficient and safe. Topical agents activating the WNT-beta-catenin pathway such as lithium are already used in dermatological practice [Kastarinen, 2014]. Inventors herein reveal that an adapted formulation allowing effective concentration of lithium in the lower layers of the epidermis but also in the dermis is an effective approach to stimulate the differentiation of melanocytes obtained in the ex vivo model using lithium treatment as herein described.

Taken together, inventors results show that the immune reaction in vitiligo occurs only at very low-level, in particular with an increased CXCL10 expression in non-depigmented skin and in peri lesional skin, while immune reaction is no longer detectable in vitiligo lesion without remaining melanocytes.

They also shed light on the previously unrecognized defect on WNT/beta-catenin activation triggered by oxidative stress that prevents the differentiation of melanocyte stem cells (FIG. 8). In addition to the better understanding of the complex pathophysiology of vitiligo, these results provide new therapeutic options to be confirmed in clinical trials.

REFERENCES

Bakis-Petsoglou, 2009
Bellei, 2013
Benson N R, et al., "An analysis of select pathogenic messages in lesional and non-lesional psoriatic skin using non-invasive tape harvesting". J Invest Dermatol. 2006 October; 126(10): 2234-41
Cavalié, J Invest Derm in Press
Chatterjee, 2014
De Jongh, 2007
Dell'Anna, 2007
Gearing, 1990
Harlow et al. (Antibodies: A laboratory Manual, CSH Press, 1988)
Harris, 2012
Janssens, 2009
Jin, 2012
Kastarinen, 2014
Kezic, 2012
Kohler et al. (Nature 256 (1975) 495
Lepe, 2003
Mosenson, 2013
Ongenae K et al. 2006
Ortonne J P 2005
Ostovari, 2004
Passeron, 2004
Passeron, 2012
Radtke, 2009
Rashighi, 2014
Schallreuter, 1995
Schallreuter, 2013
Shin, 2004
Silverberg, 2013
Schmitt, 2011
Spritz 2007
Spritz, 2012
Taieb, 2013
Thangapazham, 2014
Toosi, 2012
Ward et al. (Nature 341 (1989) 544)
Wong R et al., "Use of RT-PCR and DNA microarrays to characterize RNA recovered by non-invasive tape harvesting of normal and inflamed skin". J Invest Dermatol. 2004 July; 123(1):159-67 Wong R et al., "Analysis of RNA recovery and gene expression in the epidermis using non-invasive tape stripping"; J Dermatol Sci. 2006 November; 44(2):81-92
Yamada, 2013
Yamaguchi, 2007
Yamaguchi, 2008
Yu, 2012

The invention claimed is:

1. A method for treating Vitiligo disorder and/or repigmenting a Vitiligo lesion in a subject by inducing differentiation of melanocyte stem cells, comprising administering to the subject in need thereof an activator of at least one protein of the WNT signalling pathway selected from MITF (Microphthalmia-associated transcription factor) and PAX3 (transcription factor 3 of the paired box (PAX) family) in an amount sufficient to induce differentiation of melanocyte stem cells, wherein the activator is SKL2001.

2. The method of claim 1 wherein said at least one protein of the WNT signaling pathway is PAX3 (transcription factor 3 of the paired box (PAX) family).

3. The method of claim 1 wherein said activator is administered to the subject topically.

4. The method according to claim 1 wherein the subject has a hypopigmented area resistant to phototherapy, topical steroid or calcineurin inhibitor.

5. The method according to claim 4 wherein said resistant area is located on glabrous skin.

6. The method according to claim 5 wherein said glabrous skin is on hands or feet.

* * * * *